US009695402B2

(12) United States Patent
Seger et al.

(10) Patent No.: US 9,695,402 B2
(45) Date of Patent: Jul. 4, 2017

(54) ERK-DERIVED PEPTIDES AND USES THEREOF

(71) Applicant: Yeda Research and Development Co. Ltd., Rehovot (IL)

(72) Inventors: Rony Seger, Rehovot (IL); Alexander Plotnikov, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 15/022,280

(22) PCT Filed: Sep. 15, 2014

(86) PCT No.: PCT/IL2014/050822
§ 371 (c)(1),
(2) Date: Mar. 16, 2016

(87) PCT Pub. No.: WO2015/040609
PCT Pub. Date: Mar. 26, 2015

(65) Prior Publication Data
US 2016/0340655 A1    Nov. 24, 2016

Related U.S. Application Data

(60) Provisional application No. 61/878,633, filed on Sep. 17, 2013.

(51) Int. Cl.
*A61K 38/12* (2006.01)
*C12N 9/12* (2006.01)
*A61K 38/00* (2006.01)

(52) U.S. Cl.
CPC ............... *C12N 9/12* (2013.01); *A61K 38/12* (2013.01); *C12N 9/1205* (2013.01); *C12Y 207/11* (2013.01); *A61K 38/00* (2013.01)

(58) Field of Classification Search
None
See application file for complete search history.

(56) References Cited

U.S. PATENT DOCUMENTS

| 6,030,822 | A | 2/2000 | Lechner et al. |
| 6,090,784 | A | 7/2000 | Warren |
| 6,713,606 | B1 | 3/2004 | Smith et al. |
| 2003/0083261 | A1 | 5/2003 | Yu et al. |
| 2004/0091966 | A1 | 5/2004 | Zeidler et al. |
| 2004/0253578 | A1 | 12/2004 | Roberts et al. |
| 2006/0127891 | A1 | 6/2006 | McSwiggen et al. |
| 2010/0099627 | A1 | 4/2010 | Seger et al. |
| 2014/0212438 | A1 | 7/2014 | Seger et al. |
| 2016/0222415 | A1 | 8/2016 | Seger et al. |

FOREIGN PATENT DOCUMENTS

| WO | WO 97/20031 | 6/1997 |
| WO | WO 98/02454 | 1/1998 |
| WO | WO 99/04820 | 2/1999 |
| WO | WO 99/36094 | 7/1999 |
| WO | WO 00/12114 | 3/2000 |
| WO | WO 02/051993 | 7/2002 |
| WO | WO 2008/104979 | 9/2008 |
| WO | WO 2015/040609 | 3/2015 |

OTHER PUBLICATIONS

Advisory Action Before the Filing of an Appeal Brief Dated Nov. 12, 2013 From the US Patent and Trademark Office Re. U.S. Appl. No. 12/528,465.
European Search Report and the European Search Dated Jan. 26, 2015 From the European Patent Office Re. Application No. 14185916.5.
Examiner-Initiated Interview Summary Dated May 12, 2014 From the US Patent and Trademark Office Re. U.S. Appl. No. 12/528,465.
International Preliminary Report on Patentability Dated Jul. 29, 2010 From the International Bureau of WIPO Re. Application No. PCT/IL2008/000249.
International Preliminary Report on Patentability Dated Mar. 31, 2016 From the International Bureau of WIPO Re. Application No. PCT/IL2014/050822.
International Search Report and the Written Opinion Dated Jul. 6, 2010 From the International Searching Authority Re. Application No. PCT/IL08/00249.
International Search Report and the Written Opinion Dated Dec. 17, 2014 From the International Searching Authority Re. Application No. PCT/IL2014/050822.
Office Action Dated Dec. 29, 2013 From the Israel Patent Office Re. Application No. 219783 and Its Translation Into English.
Office Action Dated Oct. 29, 2014 From the Israel Patent Office Re. Application No. 219783 and Its Translation Into English.
Official Action Dated Aug. 6, 2013 From the US Patent and Trademark Office Re. U.S. Appl. No. 12/528,465.
Official Action Dated Sep. 7, 2011 From the US Patent and Trademark Office Re. U.S. Appl. No. 12/528,465.
Official Action Dated Nov. 9, 2011 From the US Patent and Trademark Office Re. U.S. Appl. No. 12/528,465.
Official Action Dated Mar. 13, 2015 From the US Patent and Trademark Office Re. U.S. Appl. No. 14/243,923.
Official Action Dated May 15, 2012 From the US Patent and Trademark Office Re. U.S. Appl. No. 12/528,465.
Official Action Dated Mar. 20, 2013 From the US Patent and Trademark Office Re. U.S. Appl. No. 12/528,465.
Official Action Dated Aug. 24, 2015 From the US Patent and Trademark Office Re. U.S. Appl. No. 14/243,923.
Official Action Dated Nov. 29, 2011 From the US Patent and Trademark Office Re. U.S. Appl. No. 12/528,465.
Restriction Official Action Dated Oct. 31, 2014 From the US Patent and Trademark Office Re. U.S. Appl. No. 14/243,923.
Supplementary European Search Report and the European Search Opinion Dated Feb. 27, 2014 From the European Patent Office Re. Application No. 08710249.7.

(Continued)

*Primary Examiner* — Fred Reynolds

(57) ABSTRACT

An isolated peptide being no longer than 20 amino acids comprising a sequence at least 95% homologous to the sequence GQLNHILGILGX$_1$PX$_2$QED (SEQ ID NO: 4), wherein X$_1$ and X$_2$ are any amino acid, the peptide being capable of preventing extracellular signal-regulated kinase1/2 (ERK) translocation into the nucleus.

19 Claims, 25 Drawing Sheets
(14 of 25 Drawing Sheet(s) Filed in Color)

(56) References Cited

OTHER PUBLICATIONS

Adachi et al. "Two Co-Existing Mechanisms for Nuclear Import of MAP Kinase: Passive Diffusion of a Monomer and Active Transport of a Dimer", The EMBO Journal, 18(19): 5347-5358, 1999.

Boulton et al. "REcName: Full=Mitogen-Activated Protein Kinase 1; Short=MAP Kinase 1; Short:MAPK 1; AltName: Full=ERT1; AltName: Full-Extracellular Signal-Regulated Kinase 2; Short=ERK-2; AltName: Full=MAP Kinase Isoform P42; Short=P42-MAPK; AltName: Full=Mitogen-Activated Protein Kianse 2; Short=MAPK Kinase 2: Short=MAPK 2", UniProtKB/Swiss-Prot [Online], UniProtKB/Swiss-Prot: P63086.3, GenBank Accession No. P63086, Dec. 11, 2013.

Chen et al. "Nuclear Localization and Regulation of ERK- and RSK-Encoded Protein Kinases", Molecular and Cellular Biology, 12(3): 915-927, Mar. 1992.

Christophe et al. "Nuclear Targeting of Proteins: How Many Different Signals?", Cellular Signalling, 12: 337-341, 2000.

Costa et al. "Dynamic Regulation of ERK2 Nuclear Translocation and Mobility in Living Cells", Journal of Cell Science, 119(23): 4952-4963, 2006.

Deeb et al. "Identification of an Integrated SV40 T/t-Antigen Cancer Signature in Aggressive Human Breast, Prostate, and Lung Carcinomas With Poor Prognosis", Cancer Research, 67(17): 8065-8080, Sep. 1, 2007.

GenBank "Importin-7 [Homo sapiens]", GenBank Submission, NCBI Reference Sequence: NP_006382.1, Retrieved From the Internet, 3 P., 1997.

Goddard et al. "High Affinity Binding of an N-Terminal Myristoylated P60src Peptide", The Journal of Biological Chemistry, 264(26): 15173-15176, Sep. 15, 1989.

Hoffmann et al. "Separation of Sets of Mono- and Diphosphorylated Peptides by Reversed-Phase High Performance Liquid Chromatography", Analytica Chimica Acta, 352: 327-333, 1997.

J?kel et al. "Importin Beta, Transportin, RanBP5 and RanBP7 Mediate Nuclear Import of Ribosomal Proteins in Mammalian Cells", The EMBO Journal, 17(15): 4491-4502, 1998.

Jaaro et al. "Nuclear Translocation of Mitogen-Activated Protein Kinase Kinase (MEK1) in Response to Mitogenic Stimulation", Proc. Natl. Acad. Sci. USA, 94: 3742-3747, Apr. 1997.

Joseph et al. "Interaction of Peptides Corresponding to Fatty Acylation Sites in Proteins With Model Membranes", The Journal of Biological Chemistry, 270(28): 16749-16755, Jul. 14, 1995.

Lorenzen et al. "Nuclear Import of Activated D-ERK by DIM-7, an Importin Family Member Encoded by the Gene Moleskin", Development, 128: 1403-1414, 2001. Abstract, p. 1403-1404.

Moroianu "Nuclear Import and Export Pathways", Journal of Cellular Biochemistry Supplements, 32/33: 76-83, 1999.

Muller et al. "TransMabs: Cell-Penetrating Antibodies, the Next Generation", Expert Opinion in Biological Therapy, 5(2): 1-5, 2005. Abstract, p. 2, § 6.

Owaki et al. "Extracellular Signal-Regulated Kinases in T Clees: Characterization of Human ERK1 and ERK2 cDNAs", Biochemical and Biophysical Research Communication, 182(3): 1416-1422, Feb. 14, 1992.

Rubinfeld et al. "Identification of a Cytoplasmic-Retention Sequence in ERK2", The Journal of Biological Chemistry, XP002981241, 274(43): 30349-30352, Oct. 22, 1999. Abstract.

Sparrow et al. "Chemical Synthesis and Biochemical Properties of Peptide Fragments of Apolipoprotein-Alanine", Proc. Natl. Acad. Sci. ISA, PNAS, 70(7): 2124-2128, Jul. 1973.

Walter et al. "Antibodies Specific for the Carboxy- and Amino-Terminal Regions of Simian Virus 40 Large Tumor Antigen", Proc. Natl. Acad. Sci. USA, 77(9): 5197-5200, Sep. 1980.

Wu et al. "Drug Targeting of a Peptide Radiopharmaceutical Through the Primate Blood-Brain Barrier In Vivo With a Monoclonal Insulin Receptor", Journal of Clinical Investigation, 100(7): 1804-1812, Oct. 1997.

Xu et al. "Distinct Domain Utilization by Smad3 and Smad4 for Nucleoporin Interaction and Nuclear Import", The Journal of Biological Chemistry, 278(43): 42569-42577, Oct. 24, 2003.

Yao et al. "Non-Regulated and Stimulated Mechanisms Cooperate in the Nuclear Accumulation of MEK1", Oncogene, 20(52):7588-7596, 2001.

Yazicioglu et al. "Mutations in ERK2 Binding Sites Affect Nuclear Entry", The Journal of Biological Chemistry, 282(39): 28759-28767, Sep. 28, 2007.

Supplementary European Search Report and the European Search Opinion Dated Jan. 10, 2017 From the European Patent Office Re. Application No. 14846055.3. (7 pages).

Mebratu et al. "How ERK1/2 Activation Controls Cell Proliferation and Cell Death is Subcellular Localization the Answer?", Cell Cycle, XP055331432, 8(8): 1168-1175, Apr. 15, 2009.

Plotnikov et al. "The Nuclear Translocation of ERK1/2 as an Anticancer Target", Nature Communicaitons, XP055331433, 6: 6685, Mar. 30, 2015.

Zehorai et al. "The Subcellular Localization of MEK and ERK—A Novel Nuclear Translocation Signal (NTS) Paves a Way to the Nucleus", Molecular and Cellular Endocrinology, XP026809642, 314(2): 213-220, Jan. 27, 2010.

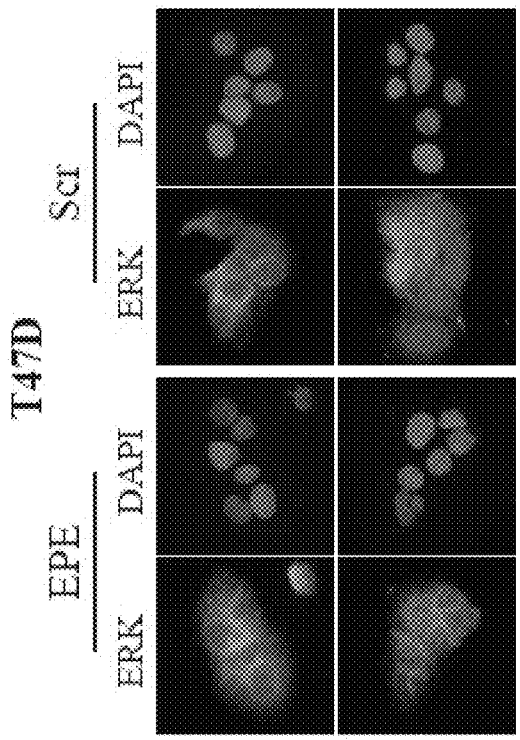
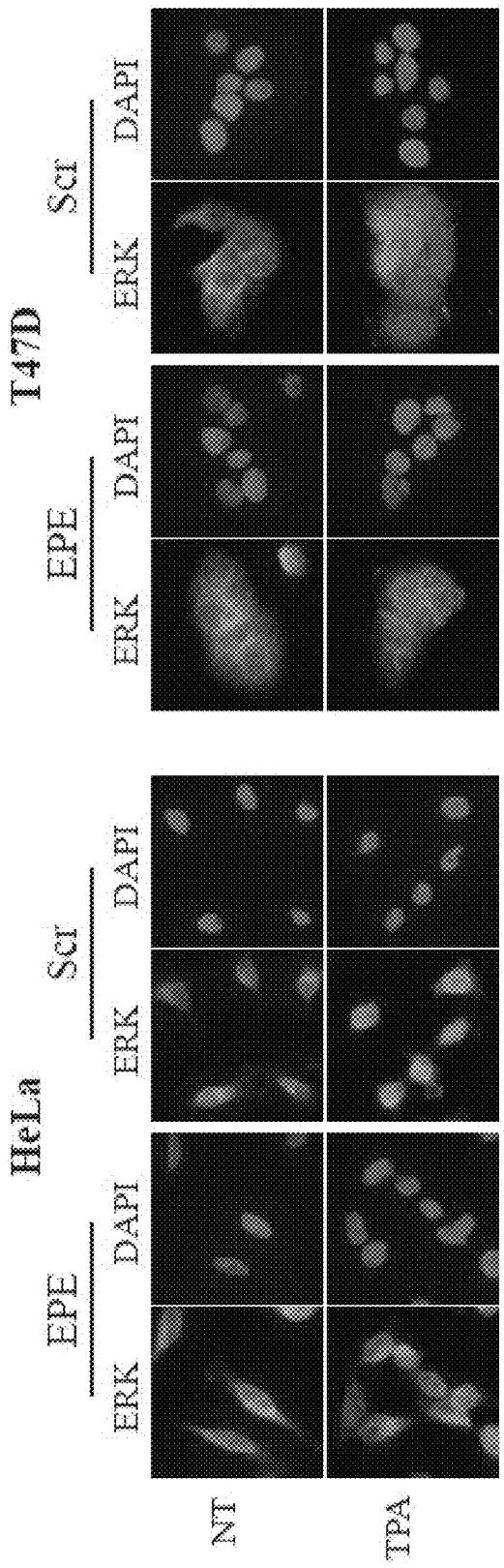

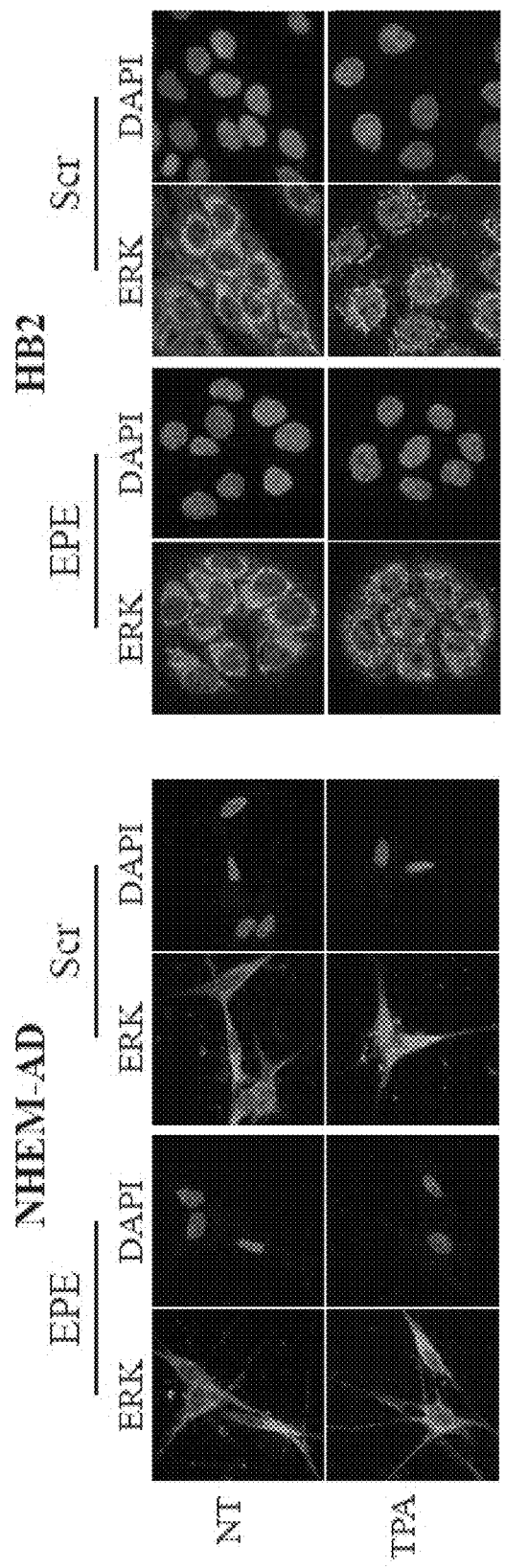

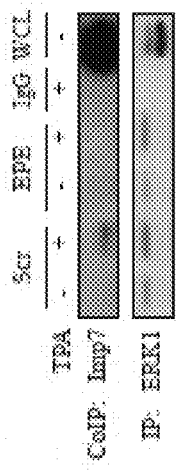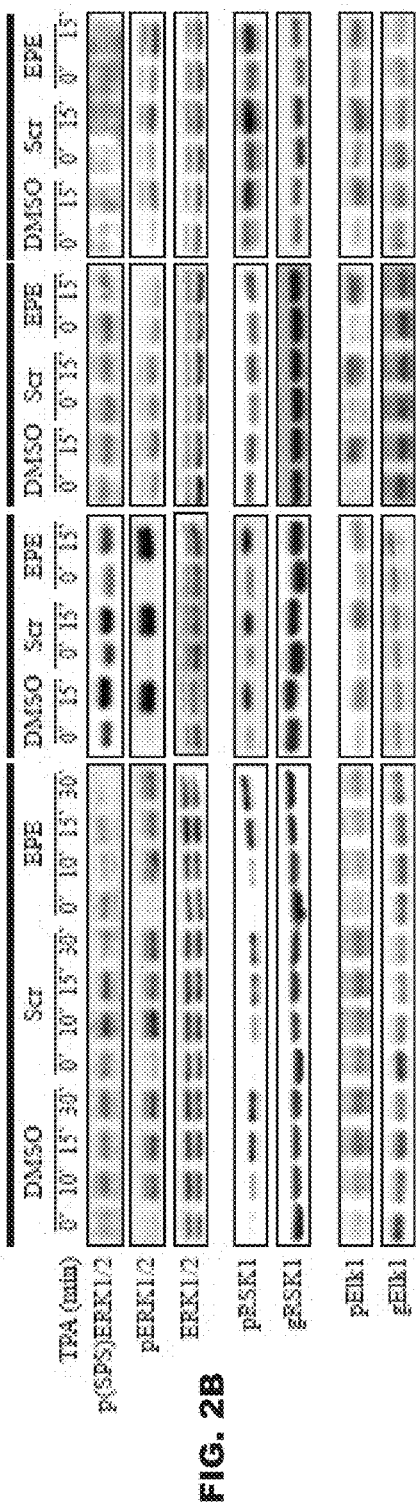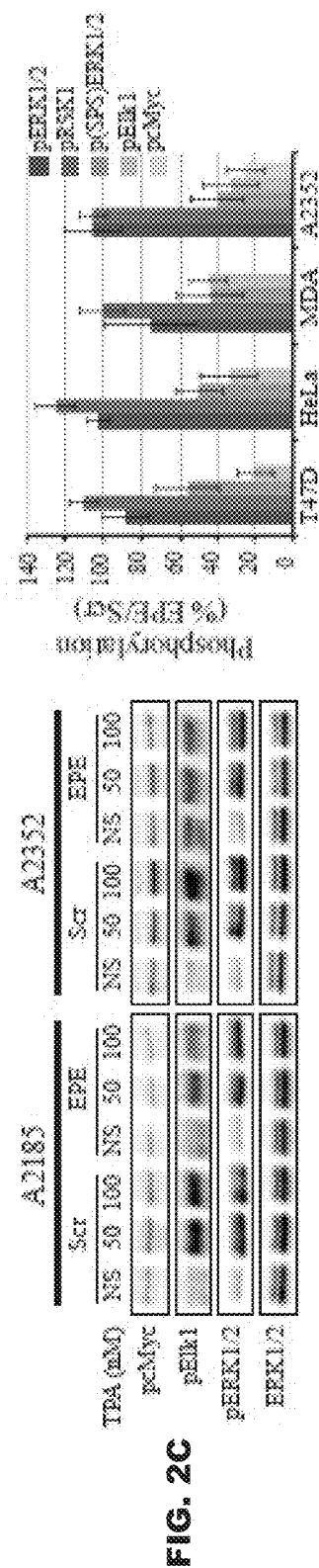
FIG. 2A
FIG. 2B
FIG. 2C
FIG. 2D

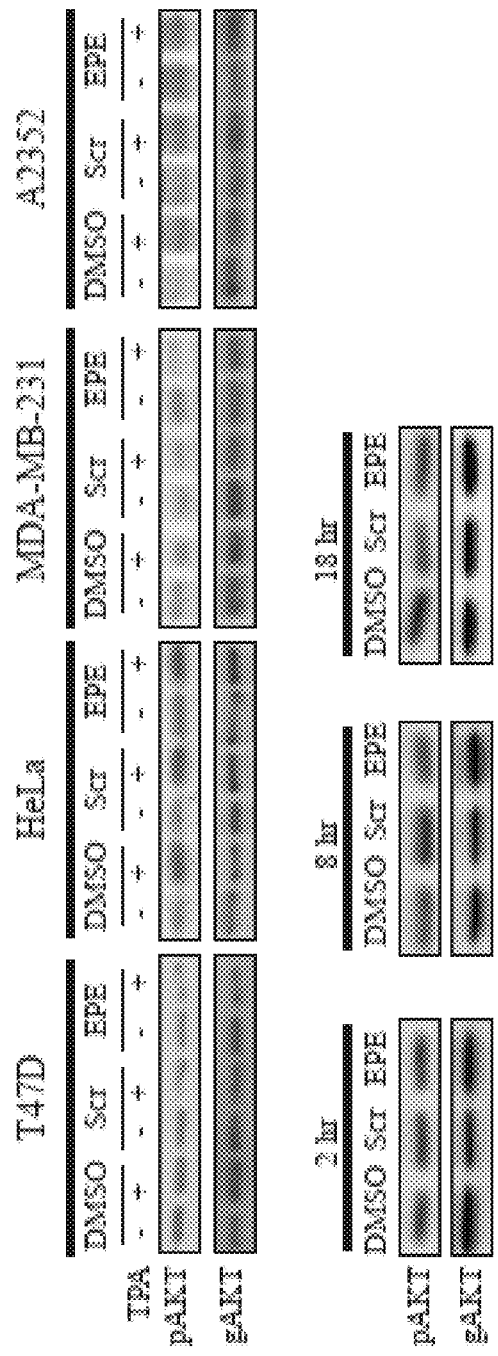

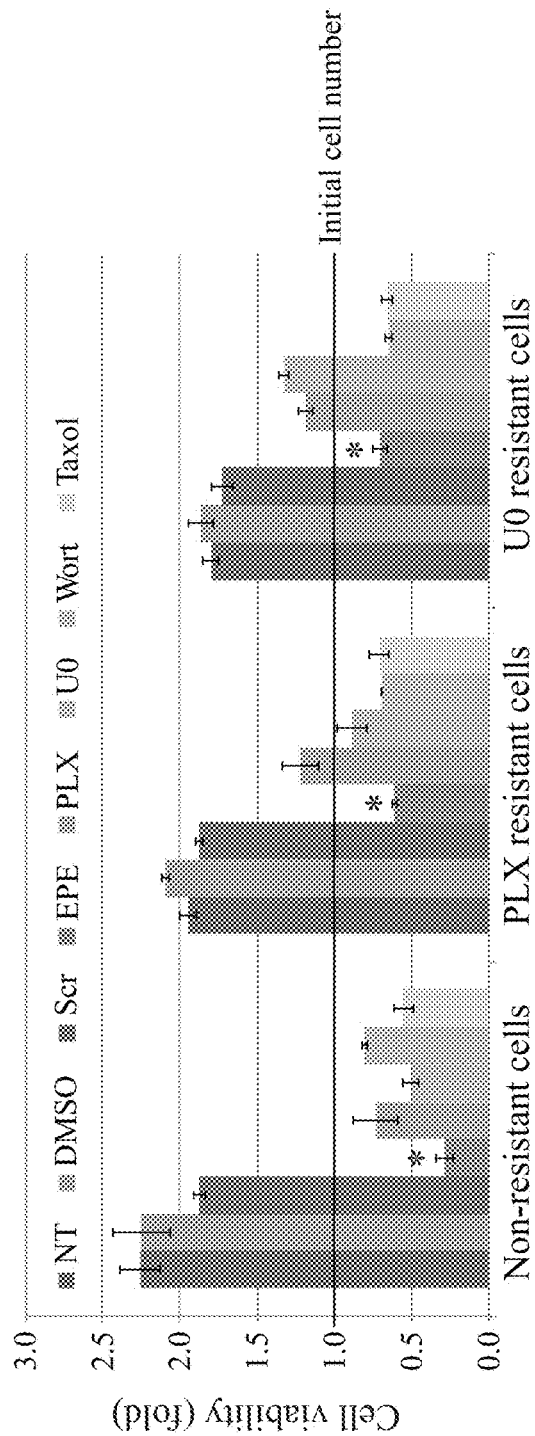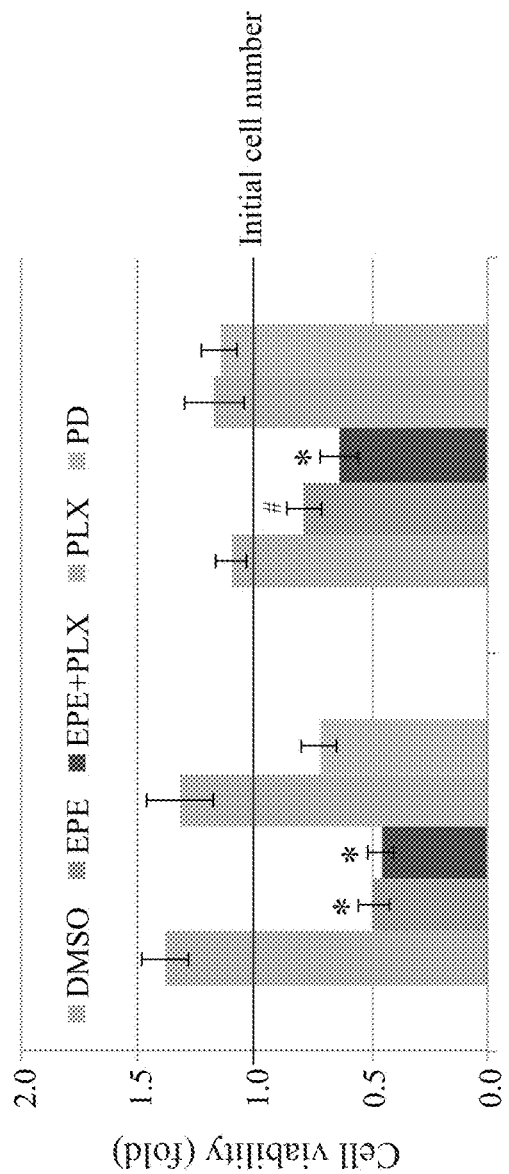
FIG. 4A
FIG. 4B

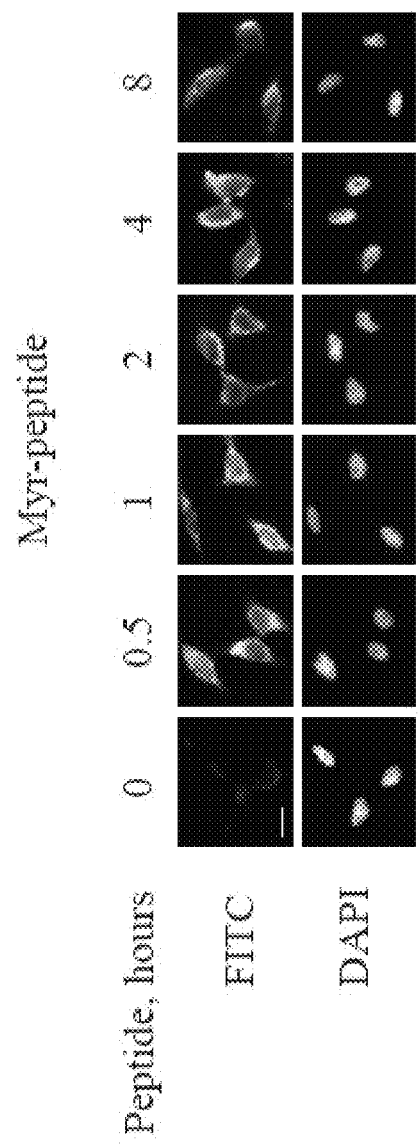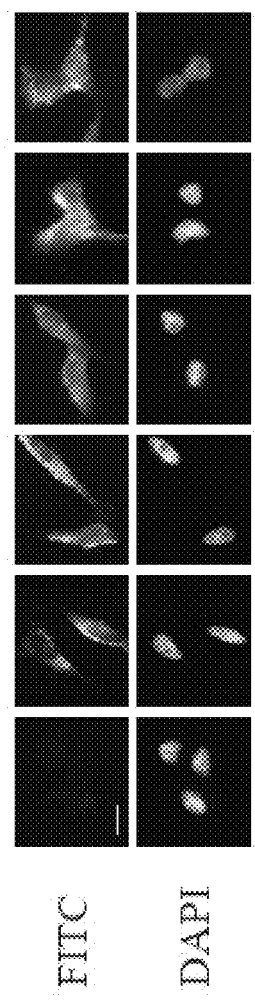
FIG. 7A
FIG. 7B

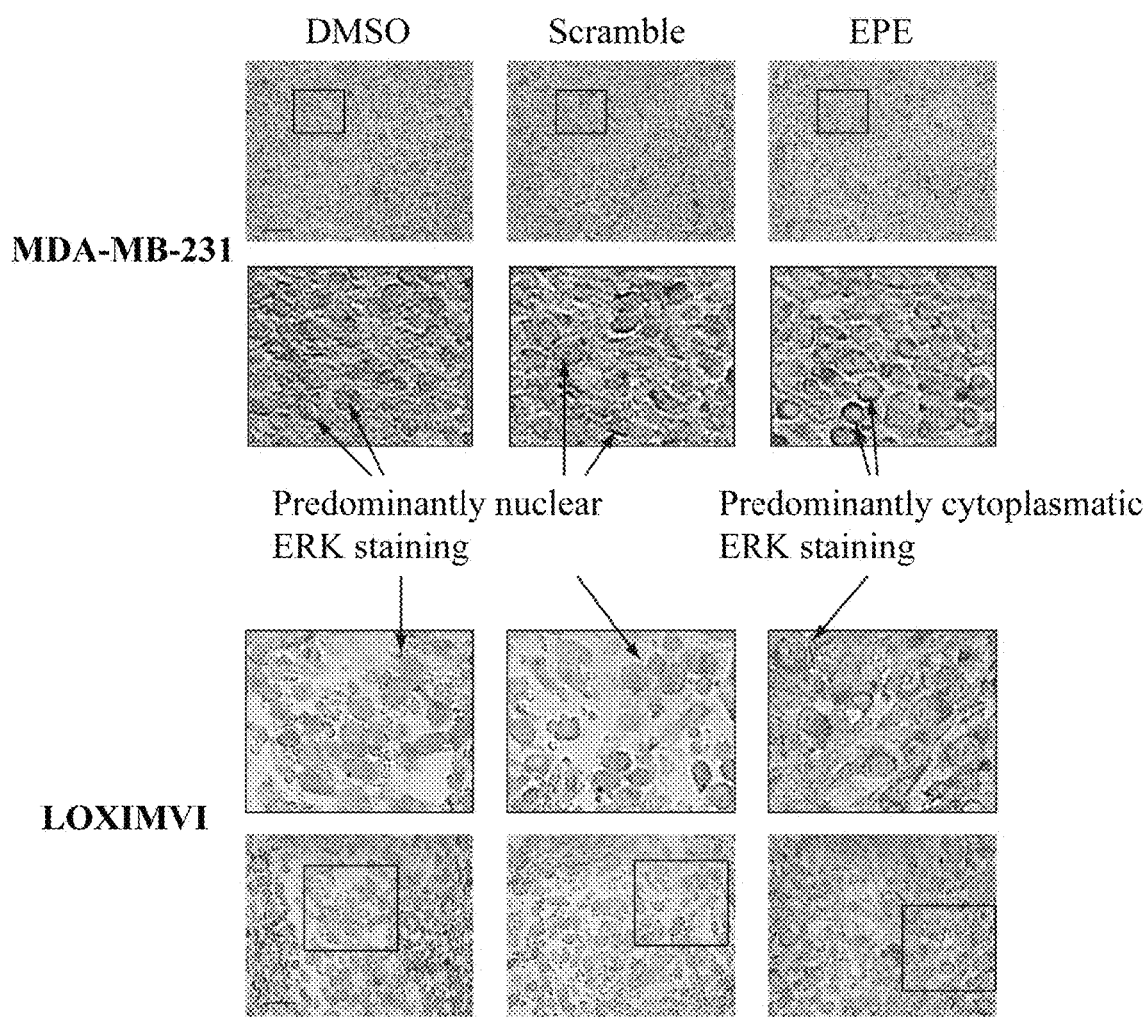

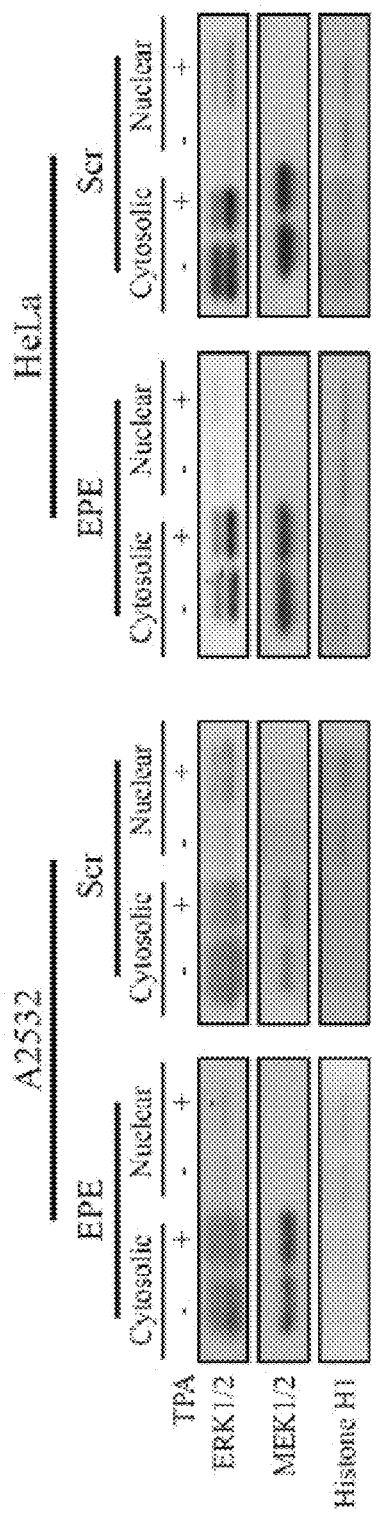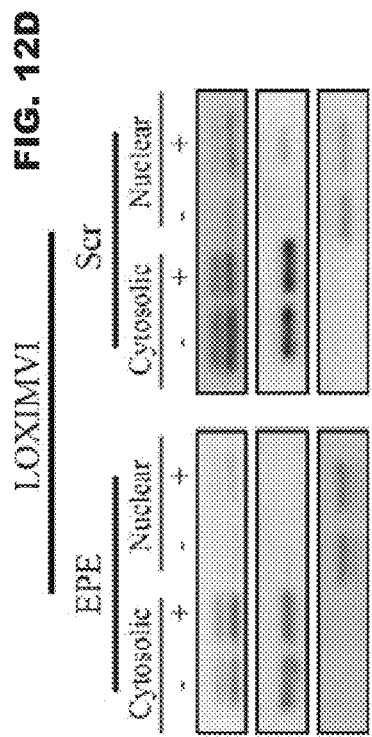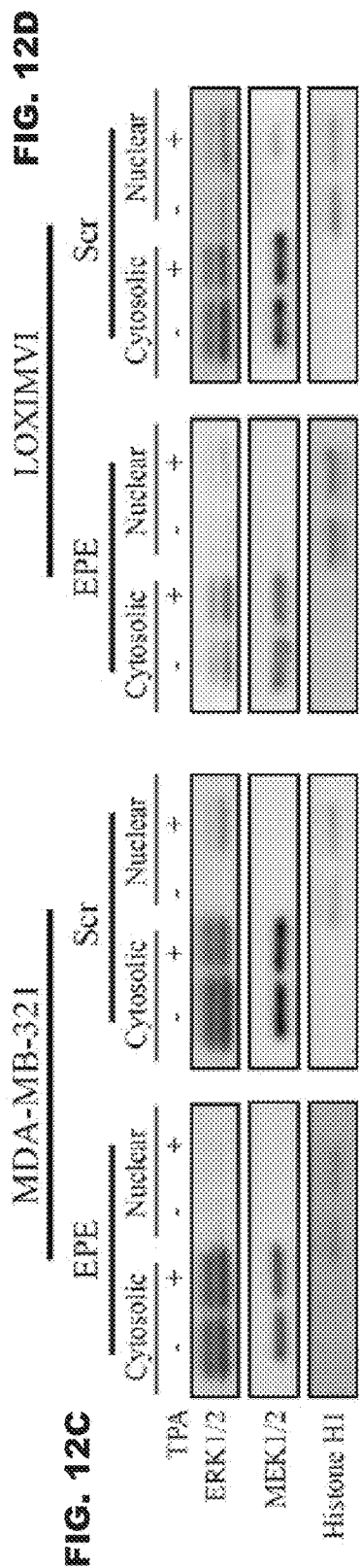

ERK-DERIVED PEPTIDES AND USES THEREOF

RELATED APPLICATIONS

This application is a National Phase of PCT Patent Application No. PCT/IL2014/050822 having International filing date of Sep. 15, 2014, which claims the benefit of priority under 35 USC §119(e) of U.S. Provisional Patent Application No. 61/878,633 filed on Sep. 17, 2013. The contents of the above applications are all incorporated by reference as if fully set forth herein in their entirety.

SEQUENCE LISTING STATEMENT

The ASCII file, entitled 65470SequenceListing.txt, created on Mar. 16, 2016, comprising 3,279 bytes, submitted concurrently with the filing of this application is incorporated herein by reference.

FIELD AND BACKGROUND OF THE INVENTION

The present invention, in some embodiments thereof, relates to peptides derived from extracellular signal-regulated kinase1/2 (ERK) which may be used for treating cancer.

The extracellular signal-regulated kinase1/2 (ERK) cascade is an intracellular signaling pathway that regulates cellular processes, such as proliferation and differentiation. Being a central signaling component, its dysregulation is involved in various pathologies, particularly cancer. Indeed, inhibitors of both Rafs and MEK1/2 within the cascade were recently developed, but despite the widespread involvement of ERK in the induction and maintenance of cancers, these inhibitors were proven beneficial almost only in B-Raf mutated melanomas. In addition, most sensitive melanomas develop resistance to the Raf/MEK inhibitors within several months of treatment. The lack of effect in many cancer types, and the mechanisms of acquired resistance are now being investigated, and shown to often involve the inhibition of ERK-dependent negative feedback loops. Consequently, this inhibition allows hyperactivation of upstream signaling components that circumvent the inhibited ERK cascade. Hence, inhibiting the ERK cascade without affecting the feedback loops should result in a more general anti cancer drug.

One of the key steps in the transmission of extracellular signals is the nuclear translocation of ERK. In resting cells, most of ERK is localized in the cytoplasm due to anchoring to cytoplasmic proteins, but stimulation causes a rapid and massive nuclear translocation of a large portion of the ERK molecules. The molecular mechanism of translocation involves first TEY-phosphorylation-dependent conformational change, which results in the detachment of the ERK molecules from their anchors. This exposes the ERK to an additional phosphorylation on two Ser residues within a nuclear translocation signal (NTS). The phosphorylation of the NTS then allows the beta-like importin (Imp), Imp7, to bind it, and consequently, induce the nuclear translocation of the kinases. This rapid translocation allows the phosphorylation and activation of many nuclear proteins, which are important for the induction and regulation of cellular processes.

U.S. Patent Application Publication No. 20100099627 teaches 18 amino acid peptides that are capable of preventing ERK translocation into the nucleus.

SUMMARY OF THE INVENTION

According to an aspect of some embodiments of the present invention there is provided an isolated peptide being no longer than 20 amino acids comprising a sequence at least 95% homologous to the sequence GQLNHILGILGX$_1$PX$_2$QED (SEQ ID NO: 4), wherein X$_1$ and X$_2$ are any amino acid, the peptide being capable of preventing extracellular signal-regulated kinase1/2 (ERK) translocation into the nucleus.

According to an aspect of some embodiments of the present invention there is provided an isolated peptide being 17 amino acids comprising the sequence GQLNHILGILGX$_1$PX$_2$QED (SEQ ID NO: 4), wherein X$_1$ and X$_2$ are any amino acid, the peptide being capable of preventing ERK translocation into the nucleus.

According to an aspect of some embodiments of the present invention there is provided a composition of matter comprising the isolated peptide described herein, attached to a cell penetrating agent.

According to an aspect of some embodiments of the present invention there is provided a method of treating cancer in a subject in need thereof comprising administering to the subject a therapeutically effective amount of the peptide described herein, thereby treating the cancer.

According to an aspect of some embodiments of the present invention there is provided a method of treating cancer in a subject in need thereof comprising administering to the subject a therapeutically effective amount of the composition of matter described herein, thereby treating the cancer.

According to an aspect of some embodiments of the present invention there is provided a pharmaceutical composition comprising the peptide described herein as an active agent and a pharmaceutically acceptable carrier.

According to an aspect of some embodiments of the present invention there is provided a pharmaceutical composition comprising the composition of matter described herein as the active agents and a pharmaceutically acceptable carrier.

According to some embodiments of the invention, the isolated peptide is 17 amino acids long.

According to some embodiments of the invention, X$_1$ and X$_2$ are each independently selected from the group consisting of glutamic acid, aspartic acid, alanine and serine.

According to some embodiments of the invention, X$_1$ and X$_2$ are each independently selected from the group consisting of glutamic acid and aspartic acid.

According to some embodiments of the invention, X$_1$ and X$_2$ are glutamic acid.

According to some embodiments of the invention, X$_1$ and X$_2$ are aspartic acid.

According to some embodiments of the invention, the isolated peptide is devoid of the amino acid sequence Leu-Aspartic acid.

According to some embodiments of the invention, neither X$_1$ nor X$_2$ is alanine.

According to some embodiments of the invention, the cell penetrating agent comprises myristic acid.

According to some embodiments of the invention, the myristic acid is attached to the N terminus of the peptide.

According to some embodiments of the invention, the cell penetrating agent is a cell penetrating peptide.

According to some embodiments of the invention, the cell penetrating peptide comprises an amino acid sequence which is attached to the N terminus of the isolated peptide described herein.

According to some embodiments of the invention, the cell penetrating peptide comprises an acid sequence as set forth in SEQ ID NO: 5.

According to some embodiments of the invention, the isolated peptide described herein is attached to the cell penetrating peptide via a peptide bond.

According to some embodiments of the invention, the isolated peptide consists of the amino acid sequence selected from the group consisting of SEQ ID NOs: 1-3, 6 and 7.

According to some embodiments of the invention, the isolated peptide attached to the cell penetrating peptide is no longer than 30 amino acids.

According to some embodiments of the invention, the peptide is attached to a cell penetrating agent.

According to some embodiments of the invention, the cancer is selected from the group consisting of melanoma, breast cancer, lung cancer, prostate cancer and cervical cancer.

According to some embodiments of the invention, the cancer is melanoma.

According to some embodiments of the invention, the melanoma comprises B-Raf melanoma.

According to some embodiments of the invention, isolated peptide is for use in treating cancer.

According to some embodiments of the invention, the composition of matter is for use in treating cancer.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-F illustrate that EPE peptide prevents nuclear translocation of ERK1. A2352 (A), MDA-MB-231 (B) HeLa (C), T47D (D), NHEM-AD (E) and HB2 (F) cells were serum-starved, pretreated with the EPE peptides, Scr peptide (10 μM, 2 h) DMSO and then either stimulated with TPA (250 nM, 15 min) or left untreated (NS) as control. The cells were stained with αgERK1/2 Ab and DAPI. Scalebar—15 μm.

FIGS. 2A-F illustrate that the EPE peptide prevents ERK1/2's NTS phosphorylation, the interaction of ERK1 with importin7 and activation of nuclear ERK1/2 targets. (A) EPE peptide prevents ERK1/2-importin7 interaction. HeLa cells were serum starved (0.1%, 16 hours), pretreated with EPE peptide, scrambled peptide (10 μM, 2 hours) or DMSO, and then stimulated with TPA (250 nM, 15 min). ERK1 were precipitated with αgERK1 Ab; importin7 co-immunoprecipitated with ERK1 was detected by WB with αimportin7 Ab. (B) EPE peptide prevents ERK1/2's NTS and Elk1 but not RSK1 phosphorylation. T47D, HeLa, MDA-MB-231 and A2352 cells were serum starved (0.1%, 16 hours), pretreated with EPE peptide, scrambled peptide (10 μM, 2 hours) or DMSO control, and then stimulated with TPA (250 nM, indicated times). Cell extracts were subjected to Western blot analysis with the indicated Abs. (C) EPE peptide inhibits phosphorylation of c-Myc and Elk1 in B-Raf melanomas. A2158 and A2352 cells were treated with scrambled and EPE peptide for two hours and then stimulated with the indicated concentration of TPA for 30 min. Cell extracts were subjected to Western blot analysis with the indicated Abs. (D) Quantification of some of the results in B and C. The bars represent fold difference between scrambled and EPE peptides in the phosphorylation of the indicated proteins after TPA stimulation. The results are the average of two or three experiments. (E) EPE-peptide does not affect short term AKT phosphorylation. The same extracts described in B were subjected to Western blot analysis using anti pAKT and gAKT Abs. (F) The EPE peptide does not affect long-term AKT phosphorylation. HeLa cells were treated with the EPE, or scrambled, peptide (10 μM) or DMSO control for the indicated times after which they were subjected to Western blot analysis using anti pAKT and gAKT Abs.

Figure 3A:
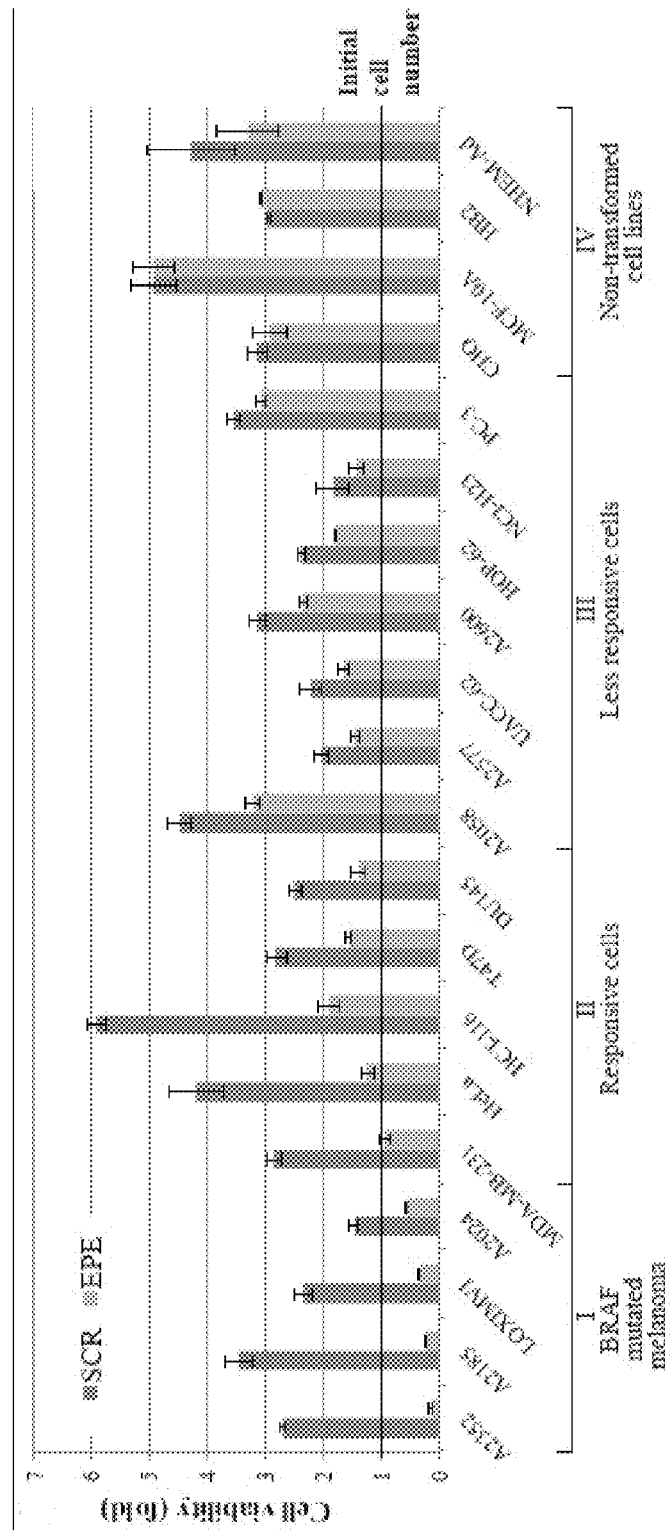
Figure 3B:
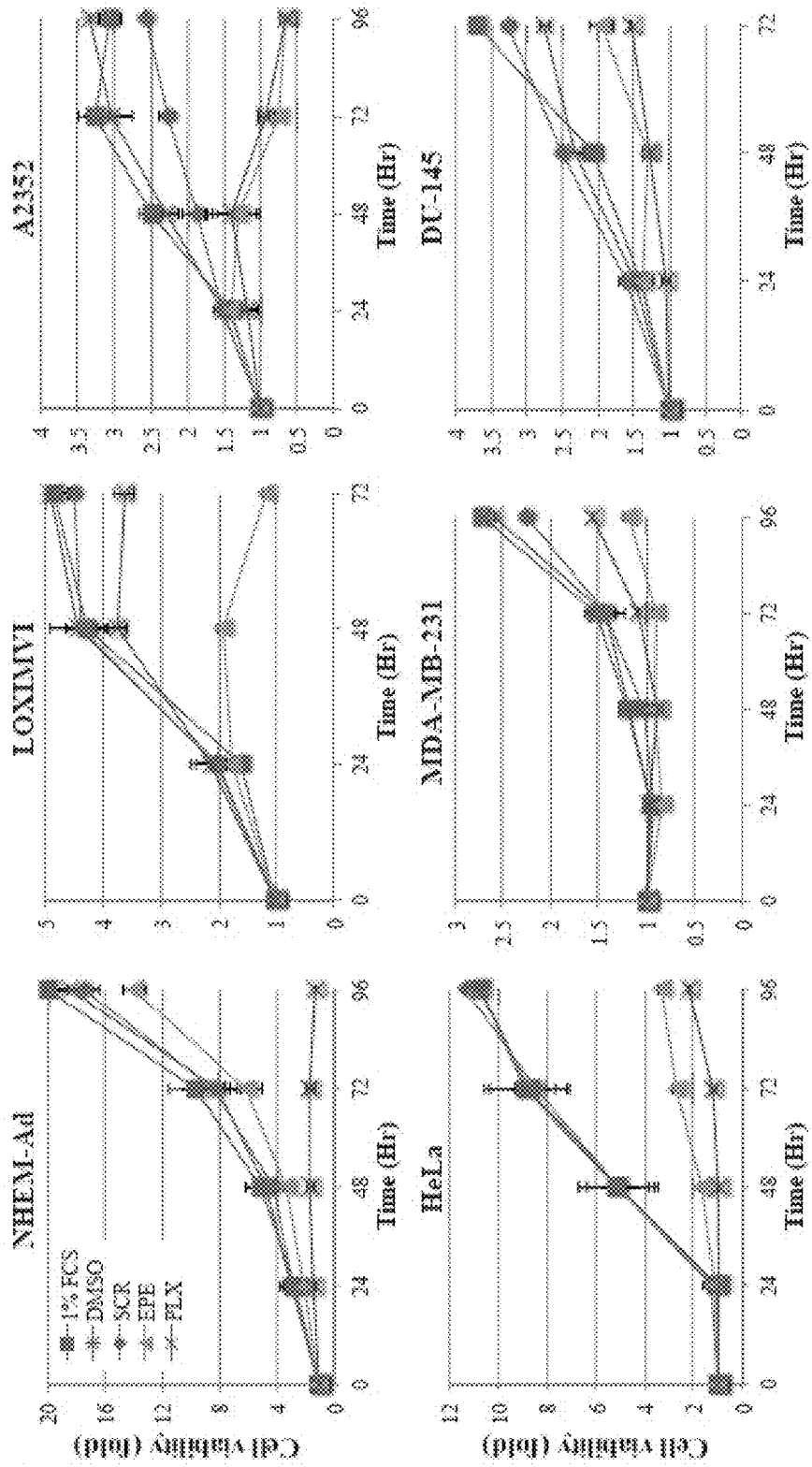

FIGS. 3A-B illustrate that EPE peptide prevents proliferation of cancer but not normal cells. (A) Effect of the EPE peptide on the proliferation of various cell lines. Sixteen cancer and four "normal" immortalized cell lines were treated with either EPE or scrambled peptides as described above. Viable cells were assayed by Methylene Blue at 48 or 72 hours after cell seeding. The data from at least three independent experiments is presented as percent of the amount of viable cells/initial cell number, where initial cell number was considered as 100. (B) Comparison of the effects of the EPE-peptide and Raf inhibitor PLX4032 on cell viability. NHEM-Ad, LOXIMVI, A2352, Hela MDA-MB-231, and DU-145 cells were treated with EPE peptide, scrambled peptide, (10 μM), PLX4032 (1 μM), DMSO control, or no treatment at 1% FCS. The number of cells was detected as above. The graphs present the kinetic of cell growth at the indicated times. All experiments were repeated 3 times in triplicates.

FIGS. 4A-B illustrate that the EPE peptide prevents proliferation of resistant melanoma cells. (A) A2352 melanoma cells resistant to either PLX4032 (B-Raf) or U0126 (MEK) inhibitors were treated with DMSO, EPE or Scr peptide (10 μM), U0126 (10 μM), PLX4032 (1 μM), Wortmannin (0.5 μM) or Taxol (25 μg/ml). Presented as percent of viable cells at 72 h/initial cell number. (B) Resistant melanomas from patients. Two vemurafenib-resistant melanoma lines, A4132 and A4168, were grown in 1% FCS and treated with medium containing DMSO, EPE peptide (10 μM), PLX4032 (1 μM), PD-184352 (5 μM) or combined treatment of EPE peptide (10 μM) plus PLX4032 (1 μM), administrating fresh medium every 24 hours during the 96 hours experiment. Methylene blue assay was performed to quantify viable cells. Experiments were done twice in triplicate. Data presented as fold change. (*) $p<0.01$, (#) $p<0.05$ with respect to the DMSO control.

FIGS. 5A-D illustrate that the EPE peptide leads to apoptosis of B-Raf mutant cancer cells. (A) The EPE peptide affects the morphology of treated cells. The indicated cells were treated with either the EPE or Scr peptides, DMSO, or taxol for 72 h, and photographed by a light microscope. (B) The EPE peptide induces apoptosis in melanoma cells detected by TUNEL. The indicated cell lines were treated as in A for 24 h. Apoptosis was detected by TUNEL staining. Images were obtained by florescence microscope. (C) Quantification of B. The bar-graph represents percent of apoptotic cells calculated in 10 different fields. (D) The EPE peptide induces apoptosis of melanoma cells detected by PARP cleavage. The indicated cell lines were treated as in (A) for 24 h. Cell extracts were subjected to Western blotting with αPARP Ab.

Figure 6A:
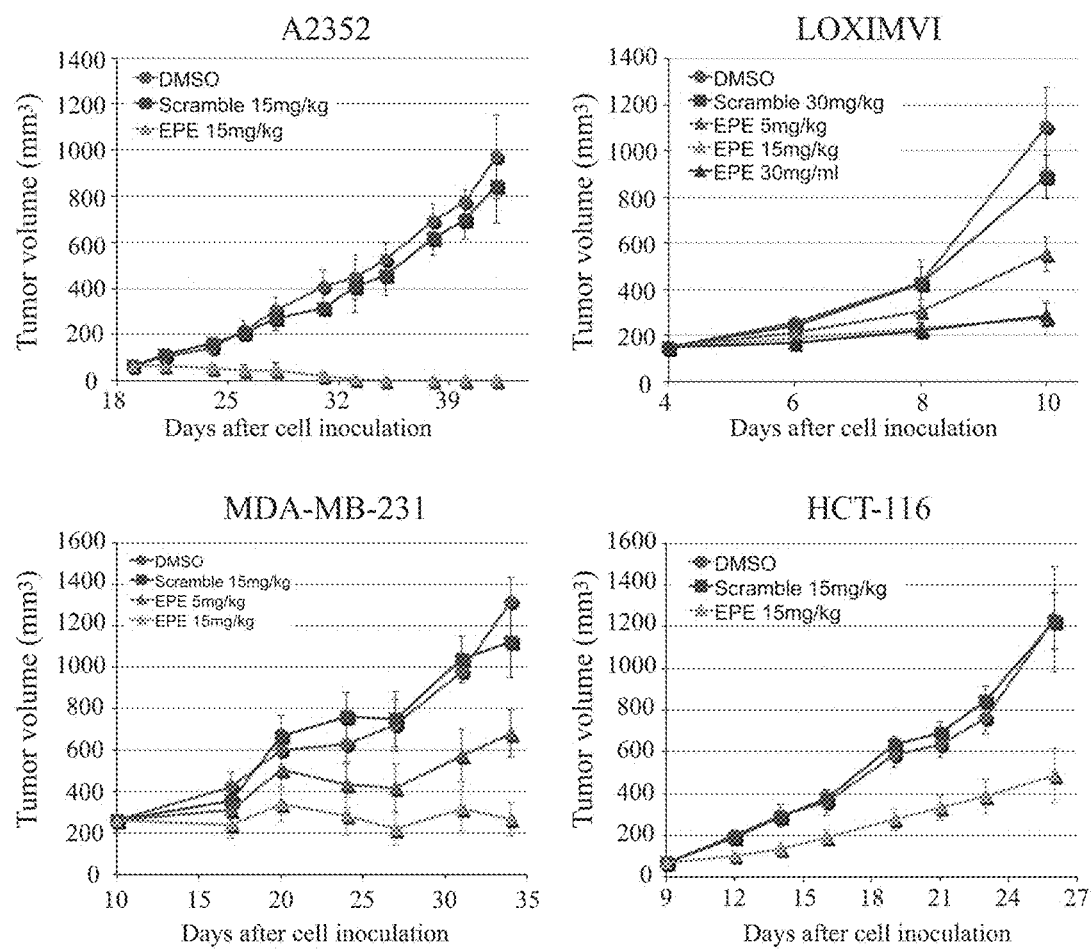
Figure 6B:
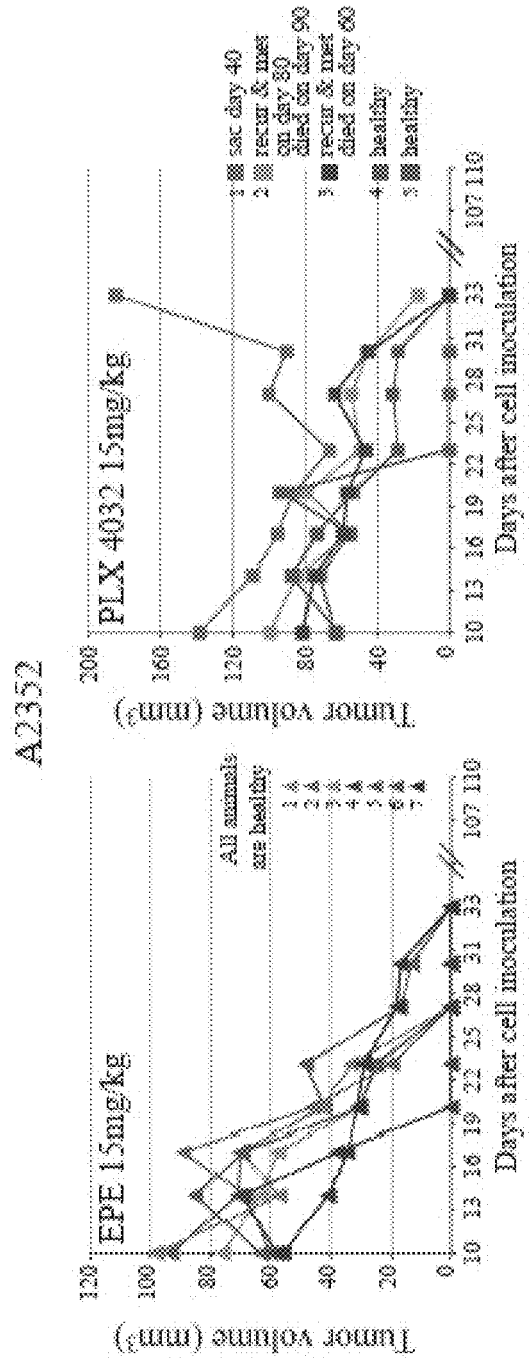

FIGS. 6A-B illustrate that the EPE peptide prevents the growth of human tumor xenografts. CD-1 nude mice were inoculated with MDA-MB-231, LOXIMVI and HCT-116 cells, and SKID mice were inoculated with A2352 cells. Upon tumors establishment, the mice were treated intravenously with the DMSO as well as EPE or Scr peptides in the indicated doses, 3 times a week. The results are averages of 5 mice in each experimental group. The X, Y, Z dimensions of the tumors were measured with a caliper, and the volume was calculated accordingly. The results are averages of 5 mice in each experimental group. The significance of all experiments was at least P<0.001. (B) The EPE peptide prevents tumor recurrence on melanoma xenograft. SCID mice were inoculated with A2352 cells. Upon establishment of tumors mice were treated intravenously with 15 mg/kg EPE peptide (n=7) or intraperitonealy with 15 mg/kg PLX4032 (n=5), at the indicated dose 3 times a week. Tumor size was recorded at the same time using a caliper. Following 3 weeks of treatment, mice were kept for further evaluation monitoring for any tumor recurrence of the effective treated melanoma xenografts. Experiment was concluded 110 days post inoculation (11 weeks after the last treatment) and the overall state of the animals was evaluated. sac=sacrificed, recur=recurrence, met=metastasis.

FIGS. 7A-B illustrate the intracellular distribution of the NTS-derived peptide. HeLa cells were serum starved, and treated for the indicated times with SPS peptide conjugated with biotin on its C terminus and either TAT (FIG. 7B) or myristic acid (FIG. 7A) on its N terminus. The intracellular distribution of the peptide was visualized using fluorescent microscope. Scale bar 15 μm.

Figure 8A:
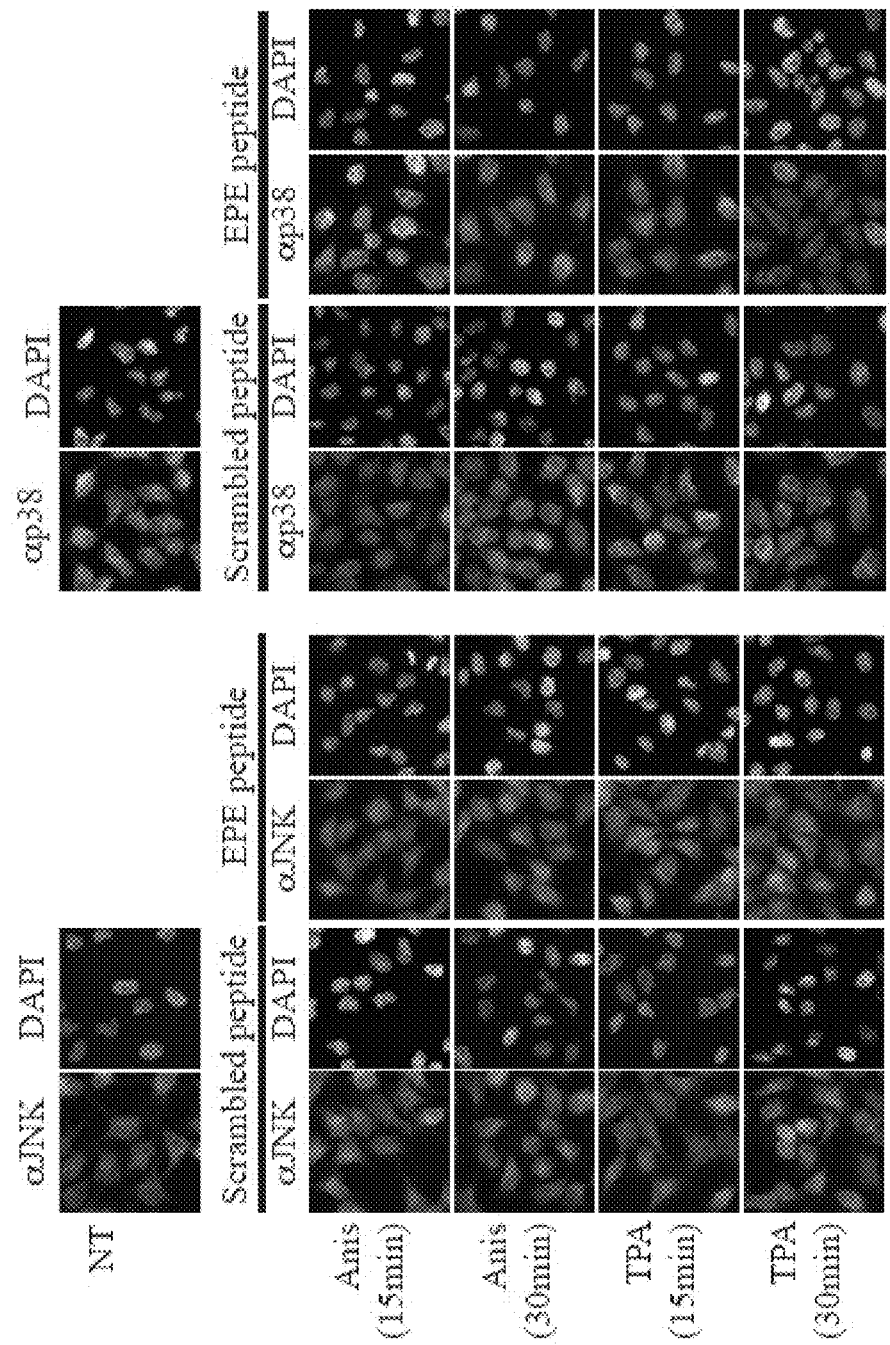
Figure 8B:
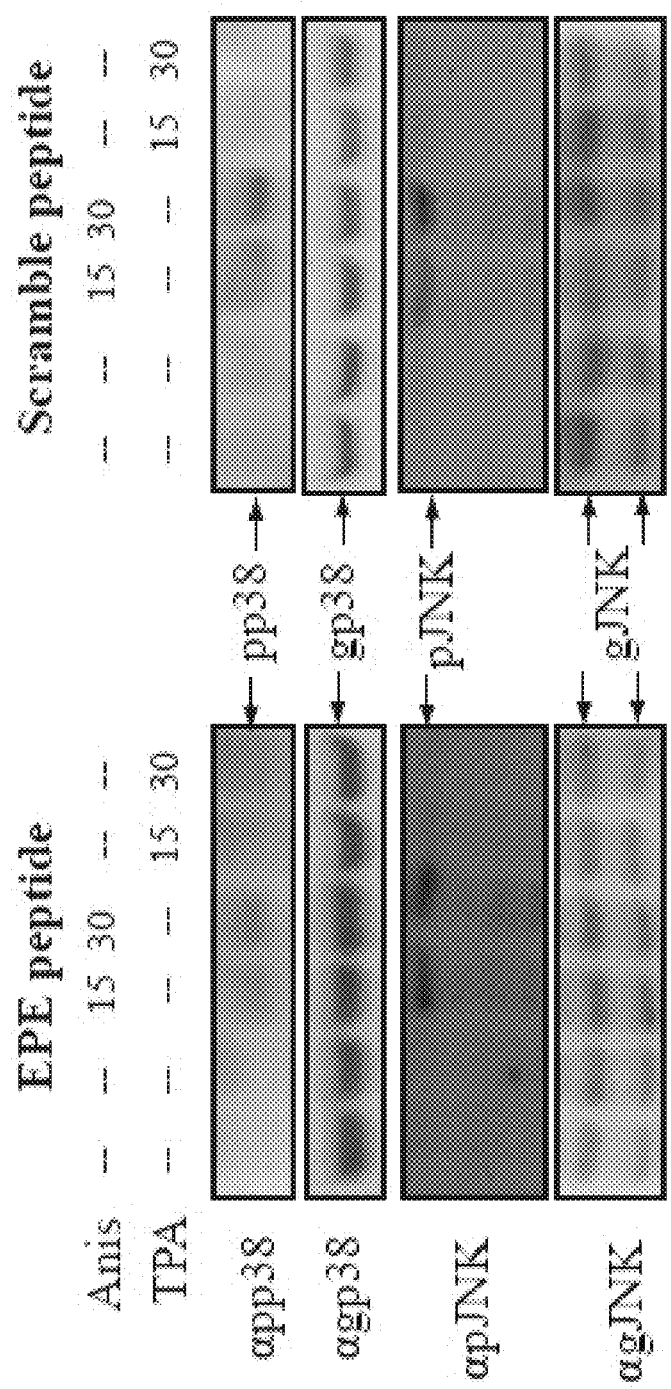

FIGS. 8A-B illustrate that the EPE peptide does not affect JNK or p38 translocation into the nucleus. (A) The EPE peptide does not affect the nuclear translocation of JNK2 and p38. HeLa cells were serum-starved, pretreated with the EPE or Scr peptides, and then stimulated with either TPA (250 nM, 15 min), anisomycin (Anis, 10 μg/ml, 15 min) for the indicated times, or left untreated as control (NT). The cells were stained with αp38 or αgJNK Abs and DAPI. Scale bar—15 μm. (B) Extracts from cells treated as in A were analyzed by Western blotting with the indicated Abs.

Figure 9B:
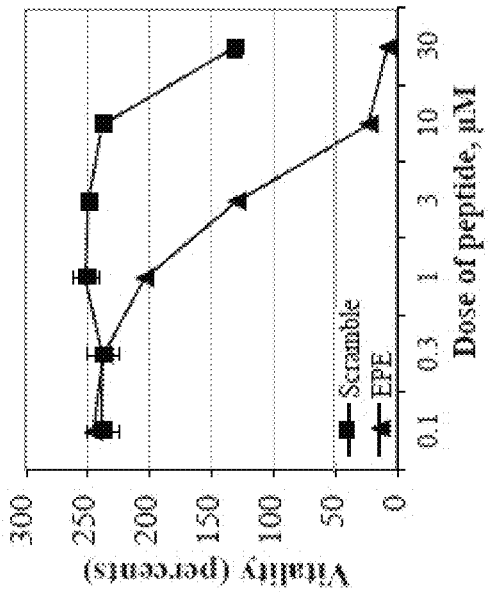
Figure 9A:
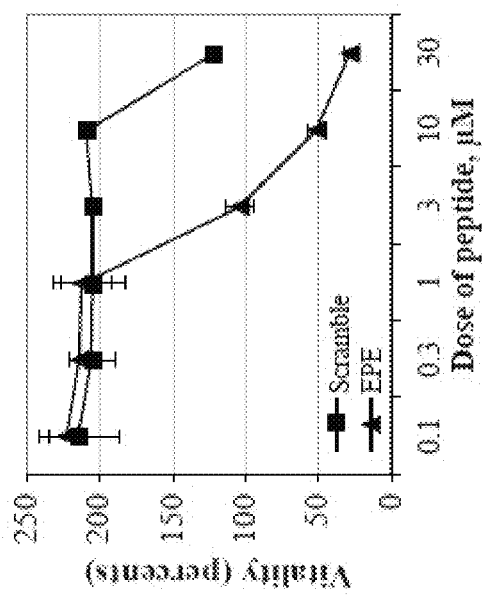

FIGS. 9A-B illustrate the dose response of the EPE peptides on melanoma cells proliferation. LOXIMVI (FIG. 9A) and A2352 (FIG. 9B) melanoma cells were treated with the indicated doses of the EPE or Scr peptides. Presented as percent of viable cells at 72 h/initial cell number.

Figure 10B:
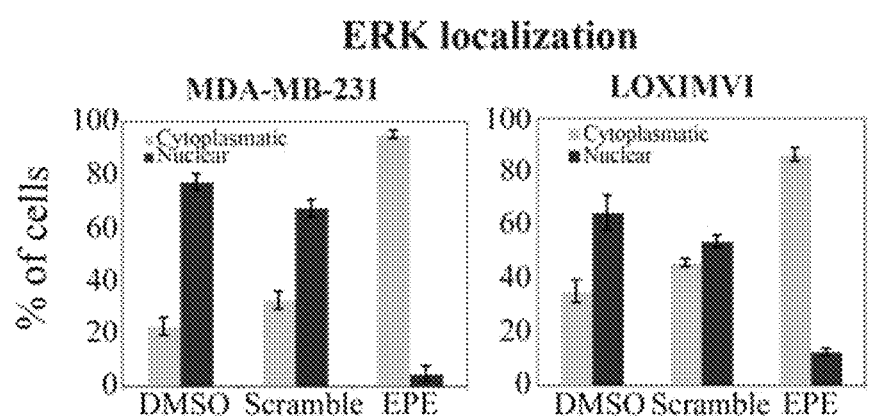

FIGS. 10A-B illustrate that the EPE peptide causes cytoplasmatic localization of ERK in xenografts. FIG. 10A: Photographs illustrating that EPE and Scr peptide as well as DMSO-treated MDA-MB-231 and LOXIMVI xenografts were immunostained with αgERK Ab. FIG. 10B presents bar-graphs representing number of cells with cytoplasmatic/nuclear ERK staining calculated in 10 random microscopic fields.

Figure 11:
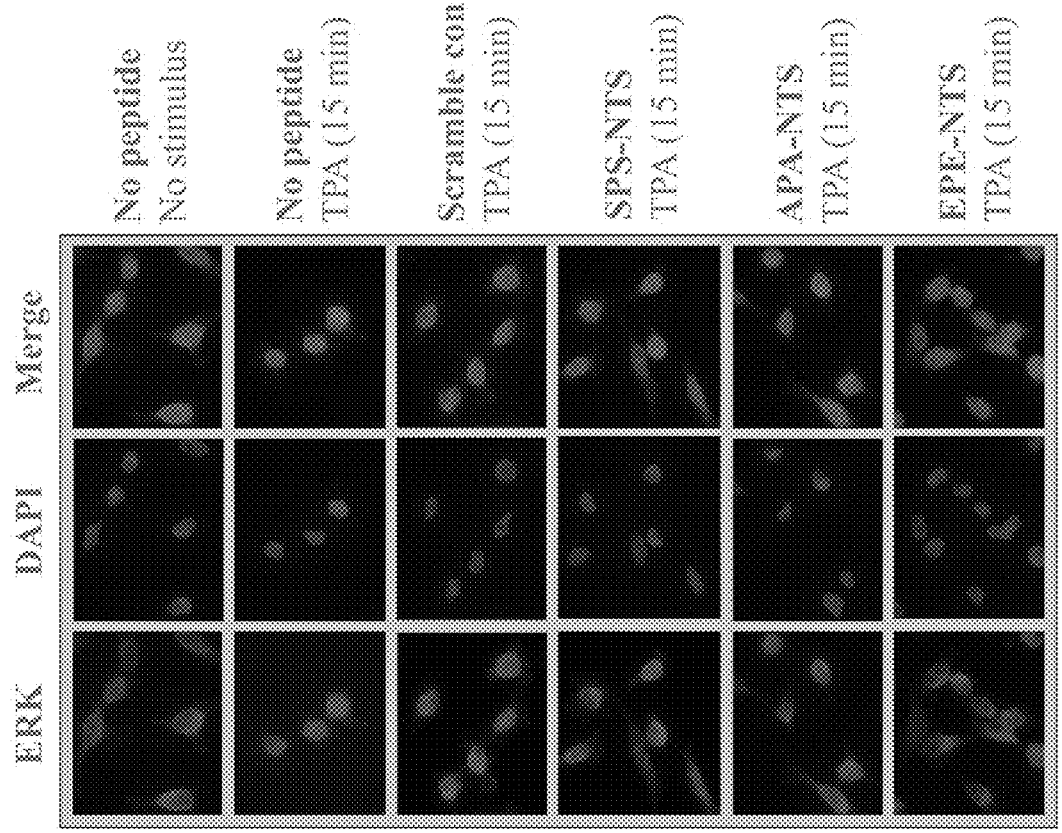

FIG. 11 illustrates that nuclear translocation of ERK1/2 is inhibited by NTS-derived peptides.

FIGS. 12A-D illustrate that the EPE peptide inhibits the nuclear translocation of ERK1/2. Serum-starved (0.1% FCS, 16 hr) A2352 (FIG. 12A), HeLa (FIG. 12B), MDA-MB-231 (FIG. 12C), or LOXMVI (FIG. 12D) cells were pretreated with EPE or scrambled peptides (10 μM, 2 hr). Cells were then stimulated with EGF (50 ng/ml) or left untreated, and then harvested. Subcellular fractionation of cytoplasm and nucleus was performed as below, and fractions were subjected to Western blot analysis with the indicated Abs. Subcellular Fractionation was performed as follows: Harvested cells were resuspended in 200 μl of buffer H containing 0.1% Nonidet P-40. The lysates were mixed vigorously and centrifuged immediately to yield supernatants containing the cytosolic fraction. Nuclear proteins were extracted by resuspending the nuclear pellets in 200 μl of extraction buffer, waiting on ice for 5 min, brief sonication (2×5 sec, 40 W, 4° C.), vigorous mixing, and centrifugation. Both cytosolic and nuclear fractions were subjected to Western blotting.

Figure 13A:
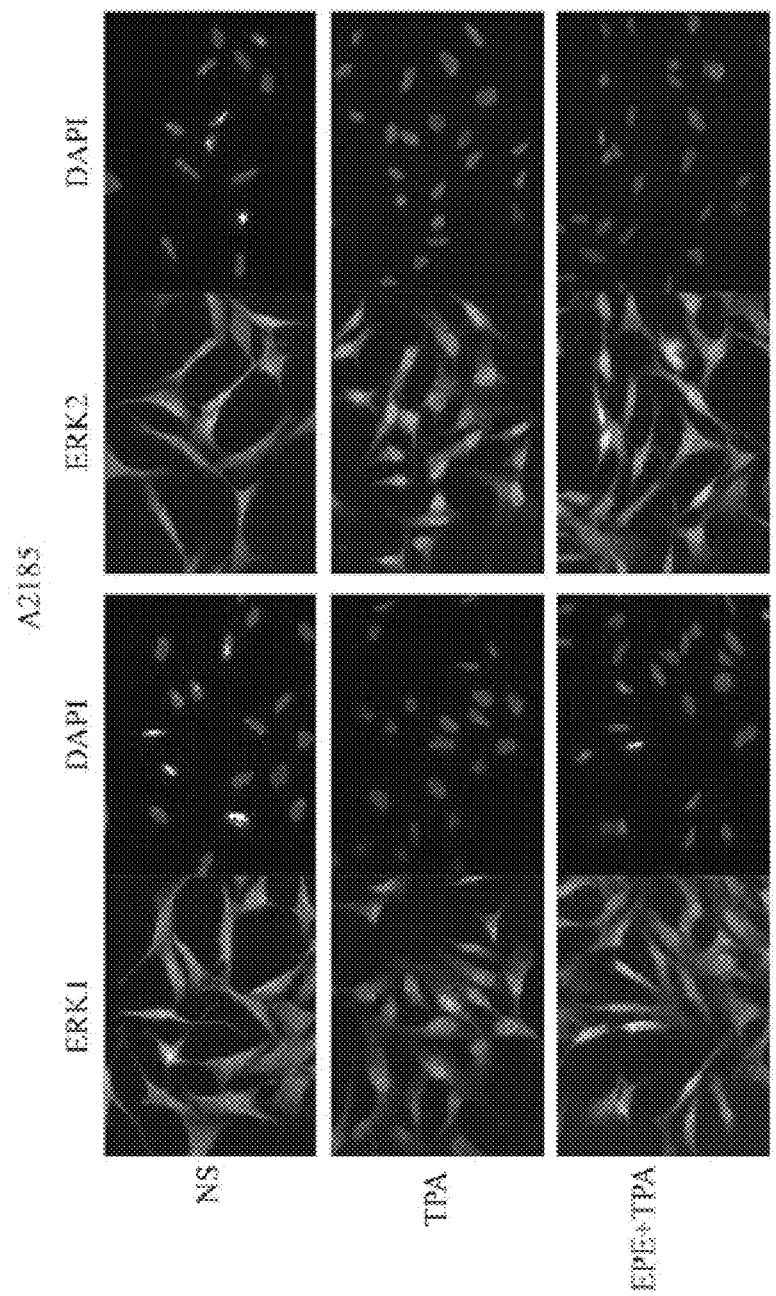
Figure 13B:
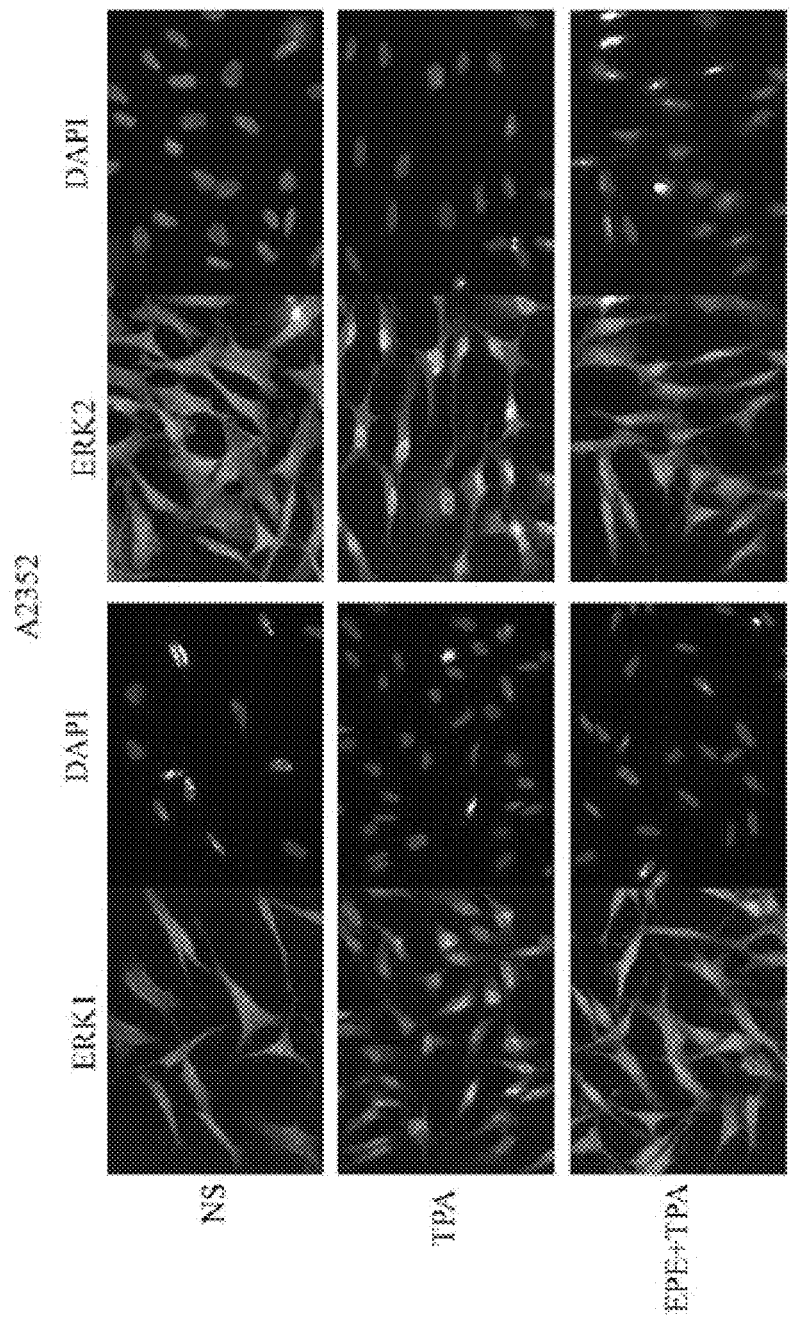
Figure 13C:
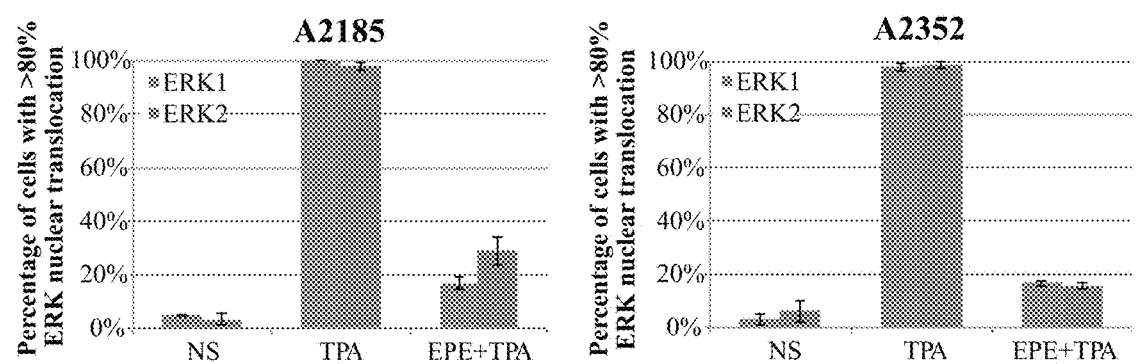

FIGS. 13A-C illustrate that the EPE peptide has a similar effect on the nuclear translocation of both ERK1 and ERK2. A2185 (A) and A2352 (B) B-Raf melanoma cells were serum-starved (16 hours, 0.1% FBS), and then either pretreated with the EPE peptides (10 μM, 2 hours) or left untreated. Then, the cells were stimulated with TPA (100 μM, 20 min), or left untreated (NS) DMSO as control. The cells were stained with either anti ERK1 (Santa Cruz, C16) or anti ERK2 (C14, Santa Cruz) Abs and DAPI. (C) Quantification of the number of cell in which ERK1 or ERK2 were mostly (>80%) localized in the nucleus was performed by counting 5 fields containing 100 cells per field.

Figure 14A:
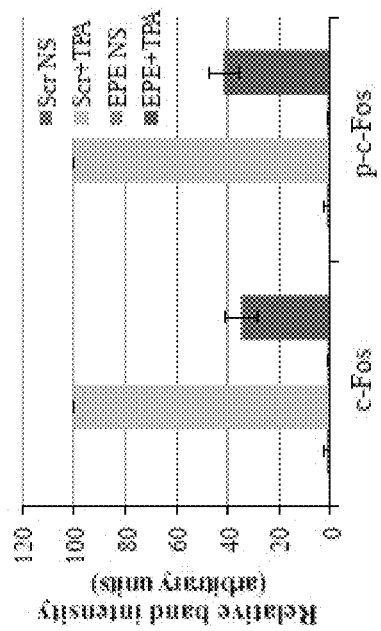
Figure 14B:
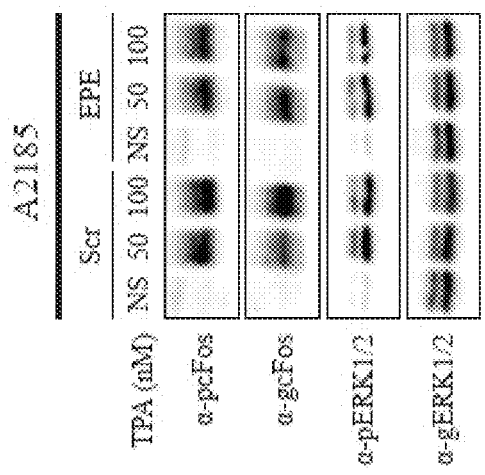

FIGS. 14A-B illustrate that the EPE peptide reduces the expression and phosphorylation of c-FOS in A2352 cells. (A) Effect of the EPE peptide on c-Fos. A2352 cells were serum starved (0.1%, 16 hours), pretreated with EPE peptide or scrambled peptide (10 μM, 2 hours), and then stimulated with TPA (50 and 100 nM, 60 min.) or left untreated (NS). Cell extracts were subjected to Western blot analysis with the indicated Abs. The anti g-c-FOS and p-c-FOS Abs were purchased from Santa Cruz (CA). (B) Quantification of the results in the 100 nM TPA in A.

Figure 15A:
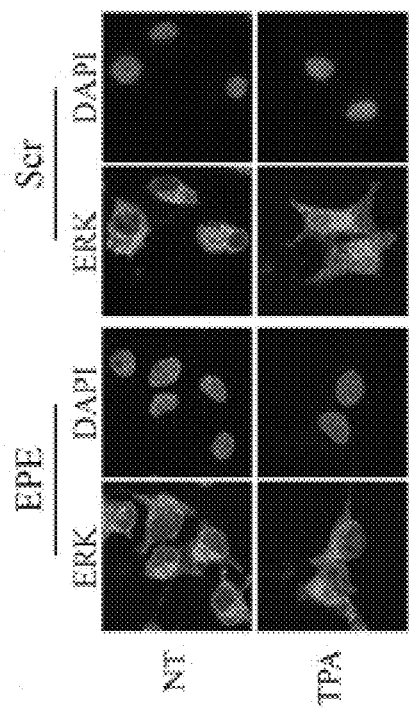
Figure 15B:
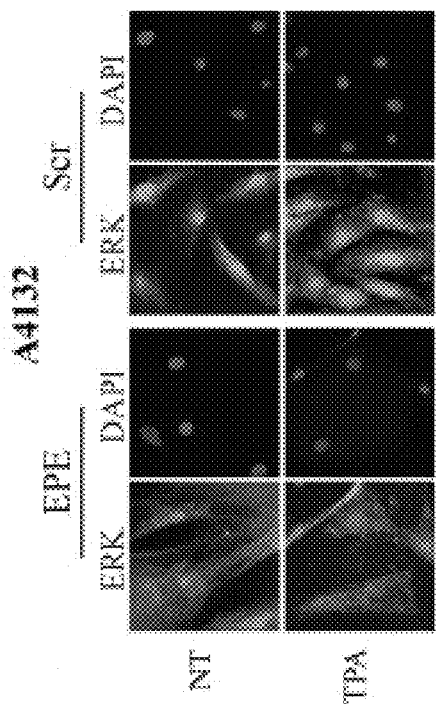

FIGS. 15A-B illustrate that the EPE peptide prevents nuclear accumulation/translocation of ERK1/2 in PLX4032-resistant melanoma cells. A2352 that were made resistant to PLX4032 (as described under Material and Methods) and A4132 PLX4032 resistant melanoma cell from patient were serum-starved (16 hours, 0.1%), pretreated with the EPE or scrambled peptide (10 μM, 2 hours) and then either stimulated with TPA (100 nM, 20 min) or left untreated (NT) as control. The cells were stained with αgERK1/2 Ab and DAPI.

DESCRIPTION OF SPECIFIC EMBODIMENTS OF THE INVENTION

The present invention, in some embodiments thereof, relates to peptides derived from extracellular signal-regulated kinase1/2 (ERK) which may be used for treating cancer.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

ERK1/2 signaling plays a crucial role in the induction of proliferation, as well as cancer development and progression. Inhibitors of the ERK cascade (e.g. vemurafenib and trametinib) serve as anti-cancer drugs. However, the majority of these agents have only a limited effect on human malignancies, and even the most effective inhibitors affect only a limited number of cancers. In addition, these inhibitors may have serious side effects including the induction of skin cancer, and the treated cancers (i.e. melanoma) develop resistance to the drugs within 6-8 months. Much of the shortcomings of the current inhibitors are probably mediated by reduced negative feedback loops.

The present inventors sought to prevent the nuclear translocation of ERK1/2, thus preventing ERK-dependent proliferation but not the negative feedback loops induced by it. The present inventors synthesized numerous peptides based on the nuclear translocation signal of ERK and showed that they were able to efficiently and specifically inhibit the interaction of ERK with Imp7, thereby preventing the nuclear translocation of ERK, without changing AKT activity that is usually enhanced by inhibition of the ERK-related negative feedback loops.

The EPE based peptide was shown to inhibit the stimulated nuclear translocation of ERK in all the cell lines examined; however, its effect on cell proliferation varied in different cell lines. The most notable effect of the peptide was on B-Raf melanoma cells, which underwent apoptosis a few hours following treatment (FIGS. 5A-D).

The application of the peptide to cultured cells induced apoptosis of melanoma cells, while inhibiting the proliferation/survival of other cancer cells, including PLX4032 and U0126-resistant melanoma cells (FIGS. 4A-B); however, it had no effect on the proliferation of immortalized cells (FIGS. 3A-B). When used in xenograft models, systemic application of the EPE peptide inhibited the growth of breast, colon and melanoma-derived tumors, and eradicated the growth of low-passage melanoma xenografts (FIGS. 6A-B and 10A-B).

Thus, according to one aspect of the present invention there is provided an isolated peptide being no longer than 20 amino acids comprising a sequence at least 95% homologous to the sequence GQLNHILGILGX$_1$PX$_2$QED (SEQ ID NO: 4), wherein X$_1$ and X$_2$ are any amino acid, the peptide being capable of preventing extracellular signal-regulated kinase1/2 (ERK) translocation into the nucleus.

The phrase "being capable of preventing extracellular signal-regulated kinase1/2 (ERK) translocation into the nucleus" refers to the ability to down-regulate the amount of ERK from translocating from the cytoplasm into the nucleus by at least 10%, 20%, 30%, 40%, 50%, 60%, 70%, 80%, 90% or more. Methods of detecting whether a peptide is capable of preventing ERK translocation are described in the Examples section, herein below.

The peptide of this aspect of the present invention may be 16, 17, 18, 19 or 20 amino acids long.

The peptide has an amino acid sequence which is typically at least 94% homologous or identical to the sequence as set forth in SEQ ID NO: 4, 95% homologous or identical to the sequence as set forth in SEQ ID NO: 4, 96% homologous or identical to the sequence as set forth in SEQ ID NO: 4, at least 97% homologous or identical to the sequence as set forth in SEQ ID NO: 4, at least 98% homologous or identical to the sequence as set forth in SEQ ID NO: 4, at least 99% homologous or identical to the sequence as set forth in SEQ ID NO: 4 or 100% homologous or identical to the sequence as set forth in SEQ ID NO: 4 as determined using the Standard protein-protein BLAST [blastp] software of the NCBI.

As mentioned, X$_1$ and X$_2$ in SEQ ID NO: 4 may be any amino acid (as specified herein below). According to one embodiment, X$_1$ and X$_2$ are each independently selected from the group consisting of glutamic acid, aspartic acid, alanine and serine. For example, the X$_1$ and X$_2$ may both be glutamic acid. For example, the X$_1$ and X$_2$ may both be aspartic acid. For example, the X$_1$ and X$_2$ may both be serine. For example, X$_1$ may be glutamic acid and X$_2$ may be aspartic acid or X$_1$ may be aspartic acid and X$_2$ may be glutamic acid. According to another embodiment, neither X$_1$ nor X$_2$ is alanine.

Thus, according to this aspect of the present invention the peptide is at least 94% homologous or identical to the sequence as set forth in SEQ ID NO: 2, 95% homologous or identical to the sequence as set forth in SEQ ID NO: 2, 96% homologous or identical to the sequence as set forth in SEQ ID NO: 2, at least 97% homologous or identical to the sequence as set forth in SEQ ID NO: 2, at least 98% homologous or identical to the sequence as set forth in SEQ ID NO: 2, at least 99% homologous or identical to the sequence as set forth in SEQ ID NO: 2 or 100% homologous or identical to the sequence as set forth in SEQ ID NO: 2 as determined using the Standard protein-protein BLAST [blastp] software of the NCBI, wherein the serine in position X$_1$ and X$_2$ is not replaceable by another amino acid.

Thus, according to this aspect of the present invention the peptide is at least 94% homologous or identical to the sequence as set forth in SEQ ID NO: 3, 95% homologous or identical to the sequence as set forth in SEQ ID NO: 3, 96% homologous or identical to the sequence as set forth in SEQ ID NO: 3, at least 97% homologous or identical to the sequence as set forth in SEQ ID NO: 3, at least 98% homologous or identical to the sequence as set forth in SEQ ID NO: 3, at least 99% homologous or identical to the sequence as set forth in SEQ ID NO: 3 or 100% homologous or identical to the sequence as set forth in SEQ ID NO: 3 as determined using the Standard protein-protein BLAST [blastp] software of the NCBI, wherein the alanine in position X$_1$ and X$_2$ is not replaceable by another amino acid.

Thus, according to this aspect of the present invention the peptide is at least 94% homologous or identical to the sequence as set forth in SEQ ID NO: 6, 95% homologous or identical to the sequence as set forth in SEQ ID NO: 6, 96% homologous or identical to the sequence as set forth in SEQ ID NO: 6, at least 97% homologous or identical to the sequence as set forth in SEQ ID NO: 6, at least 98% homologous or identical to the sequence as set forth in SEQ ID NO: 6, at least 99% homologous or identical to the sequence as set forth in SEQ ID NO: 6 or 100% homologous or identical to the sequence as set forth in SEQ ID NO: 6 as determined using the Standard protein-protein BLAST [blastp] software of the NCBI, wherein the glutamic acid in position X$_1$ and X$_2$ is not replaceable by another amino acid.

Thus, according to this aspect of the present invention the peptide is at least 94% homologous or identical to the sequence as set forth in SEQ ID NO: 7 (GQLNHILGILGD-PDQED, 95% homologous or identical to the sequence as set forth in SEQ ID NO: 7, 96% homologous or identical to the sequence as set forth in SEQ ID NO: 7, at least 97% homologous or identical to the sequence as set forth in SEQ ID NO: 7, at least 98% homologous or identical to the sequence as set forth in SEQ ID NO: 7, at least 99% homologous or identical to the sequence as set forth in SEQ ID NO: 7 or 100% homologous or identical to the sequence as set forth in SEQ ID NO: 7 as determined using the Standard protein-protein BLAST [blastp] software of the NCBI, wherein the aspartic acid in position $X_1$ and $X_2$ is not replaceable by another amino acid.

Peptides which are not 100% homologous to the sequences disclosed herein may comprise either conservative or non-conservative substitutions, deletions or additions.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered conservative substitutions.

For producing conservative substitutions by non-naturally occurring amino acids it is also possible to use amino acid analogs (synthetic amino acids) well known in the art. A peptidomimetic of the naturally occurring amino acids is well documented in the literature known to the skilled practitioner.

When effecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH[(—CH$_2$)$_5$—COOH]—CO— for aspartic acid. Those non-conservative substitutions which fall within the scope of the present invention are those which still constitute a polypeptide being able to prevent ERK translocation into the nucleus.

Preferably, the peptides of the present invention are typically devoid of the sequence Leu-Aspartic acid.

Further, preferably the N terminal amino acid of the peptide is glycine.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but not limited to N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided herein under.

Peptide bonds (—CO—NH—) within the peptide may be substituted, for example, by N-methylated amide bonds (—N(CH3)-CO—), ester bonds (—C(=O)—O—), ketomethylene bonds (—CO—CH2-), sulfinylmethylene bonds (—S(=O)—CH2-), α-aza bonds (—NH—N(R)—CO—), wherein R is any alkyl (e.g., methyl), amine bonds (—CH2-NH—), sulfide bonds (—CH2-S—), ethylene bonds (—CH2-CH2-), hydroxyethylene bonds (—CH(OH)—CH2-), thioamide bonds (—CS—NH—), olefinic double bonds (—CH=CH—), fluorinated olefinic double bonds (—CF=CH—), retro amide bonds (—NH—CO—), peptide derivatives (—N(R)—CH2-CO—), wherein R is the "normal" side chain, naturally present on the carbon atom.

These modifications can occur at any of the bonds along the peptide chain and even at several (2-3) bonds at the same time.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr.

The peptides of some embodiments of the invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1), and non-conventional or modified amino acids (e.g., synthetic, Table 2), which can be used with some embodiments of the invention.

TABLE 1

| One-letter Symbol | Three-Letter Abbreviation | Amino Acid |
|---|---|---|
| A | Ala | Alanine |
| R | Arg | Arginine |
| N | Asn | Asparagine |
| D | Asp | Aspartic acid |
| C | Cys | Cysteine |
| Q | Gln | Glutamine |
| E | Glu | Glutamic Acid |
| G | Gly | Glycine |
| H | His | Histidine |
| I | Ile | Isoleucine |
| L | Leu | Leucine |
| K | Lys | Lysine |
| M | Met | Methionine |
| F | Phe | Phenylalanine |
| P | Pro | Proline |
| S | Ser | Serine |
| T | Thr | Threonine |
| W | Trp | Tryptophan |
| Y | Tyr | Tyrosine |
| V | Val | Valine |
| X | Xaa | Any amino acid as above |

TABLE 2

| Code | Non-conventional amino acid | Code | Non-conventional amino acid |
|---|---|---|---|
| Hyp | hydroxyproline | Orn | ornithine |
| Norb | aminonorbornyl-carboxylate | Abu | α-aminobutyric acid |
| Cpro | aminocyclopropane-carboxylate | Dala | D-alanine |
| Narg | N-(3-guanidinopropyl)glycine | Darg | D-arginine |
| Nasn | N-(carbamylmethyl)glycine | Dasn | D-asparagine |
| Nasp | N-(carboxymethyl)glycine | Dasp | D-aspartic acid |
| Ncys | N-(thiomethyl)glycine | Dcys | D-cysteine |
| Ngln | N-(2-carbamylethyl)glycine | Dgln | D-glutamine |
| Nglu | N-(2-carboxyethyl)glycine | Dglu | D-glutamic acid |
| Nhis | N-(imidazolylethyl)glycine | Dhis | D-histidine |
| Nile | N-(1-methylpropyl)glycine | Dile | D-isoleucine |
| Nleu | N-(2-methylpropyl)glycine | Dleu | D-leucine |
| Nlys | N-(4-aminobutyl)glycine | Dlys | D-lysine |
| Nmet | N-(2-methylthioethyl)glycine | Dmet | D-methionine |
| Norn | N-(3-aminopropyl)glycine | Dorn | D-ornithine |
| Nphe | N-benzylglycine | Dphe | D-phenylalanine |
| Nser | N-(hydroxymethyl)glycine | Dpro | D-proline |
| Nthr | N-(1-hydroxyethyl)glycine | Dser | D-serine |
| Nhtrp | N-(3-indolylethyl) glycine | Dthr | D-threonine |
| Ntyr | N-(p-hydroxyphenyl)glycine | Dtrp | D-tryptophan |
| Nval | N-(1-methylethyl)glycine | Dtyr | D-tyrosine |
| Nmgly | N-methylglycine | Dval | D-valine |
| Nmala | L-N-methylalanine | Dnmala | D-N-methylalanine |
| Nmarg | L-N-methylarginine | Dnmarg | D-N-methylarginine |
| Nmasn | L-N-methylasparagine | Dnmasn | D-N-methylasparagine |
| Nmasp | L-N-methylaspartic acid | Dnmasp | D-N-methylasparatate |
| Nmcys | L-N-methylcysteine | Dnmcys | D-N-methylcysteine |
| Nmgln | L-N-methylglutamine | Dnmgln | D-N-methylglutamine |
| Nmglu | L-N-methylglutamic acid | Dnmglu | D-N-methylglutamate |
| Nmhis | L-N-methylhistidine | Dnmhis | D-N-methylhistidine |
| Nmile | L-N-methylisolleucine | Dnmile | D-N-methylisoleucine |
| Nmleu | L-N-methylleucine | Dnmleu | D-N-methylleucine |
| Nmlys | L-N-methyllysine | Dnmlys | D-N-methyllysine |
| Nmmet | L-N-methylmethionine | Dnmmet | D-N-methylmethionine |
| Nmorn | L-N-methylornithine | Dnmorn | D-N-methylornithine |
| Nmphe | L-N-methylphenylalanine | Dnmphe | D-N-methylphenylalanine |
| Nmpro | L-N-methylproline | Dnmpro | D-N-methylproline |
| Nmser | L-N-methylserine | Dnmser | D-N-methylserine |
| Nmthr | L-N-methylthreonine | Dnmthr | D-N-methylthreonine |
| Nmtrp | L-N-methyltryptophan | Dnmtrp | D-N-methyltryptophan |
| Nmtyr | L-N-methyltyrosine | Dnmtyr | D-N-methyltyrosine |
| Nmval | L-N-methylvaline | Dnmval | D-N-methylvaline |
| Nmnle | L-N-methylnorleucine | Nle | L-norleucine |
| Nmnva | L-N-methylnorvaline | Nva | L-norvaline |
| Nmetg | L-N-methyl-ethylglycine | Etg | L-ethylglycine |
| Nmtbug | L-N-methyl-t-butylglycine | Tbug | L-t-butylglycine |
| Nmhphe | L-N-methyl-homophenylalanine | Hphe | L-homophenylalanine |
| Nmanap | N-methyl-α-naphthylalanine | Anap | α-naphthylalanine |
| Nmpen | N-methylpenicillamine | Pen | penicillamine |
| Nmgabu | N-methyl-γ-aminobutyrate | Gabu | γ-aminobutyric acid |
| Nmchexa | N-methyl-cyclohexylalanine | Chexa | cyclohexylalanine |
| Nmcpen | N-methyl-cyclopentylalanine | Cpen | cyclopentylalanine |
| Nmaabu | N-methyl-α-amino-α-methylbutyrate | Aabu | α-amino-α-methylbutyrate |
| Nmaib | N-methyl-α-aminoisobutyrate | Aib | α-aminoisobutyric acid |
| Marg | L-α-methylarginine | Dmarg | D-α-methylarginine |
| Masn | L-α-methylasparagine | Dmasn | D-α-methylasparagine |
| Masp | L-α-methylaspartate | Dmasp | D-α-methylaspartate |
| Mcys | L-α-methylcysteine | Dmcys | D-α-methylcysteine |
| Mgln | L-α-methylglutamine | Dmgln | D-α-methylglutamine |
| Mglu | L-α-methylglutamate | Dmglu | D-α-methyl glutamic acid |
| Mhis | L-α-methylhistidine | Dmhis | D-α-methylhistidine |
| Mile | L-α-methylisoleucine | Dmile | D-α-methylisoleucine |
| Mleu | L-α-methylleucine | Dmleu | D-α-methylleucine |
| Mlys | L-α-methyllysine | Dmlys | D-α-methyllysine |
| Mmet | L-α-methylmethionine | Dmmet | D-α-methylmethionine |
| Morn | L-α-methylornithine | Dmorn | D-α-methylornithine |
| Mphe | L-α-methylphenylalanine | Dmphe | D-α-methylphenylalanine |
| Mpro | L-α-methylproline | Dmpro | D-α-methylproline |
| Mser | L-α-methylserine | Dmser | D-α-methylserine |
| Mthr | L-α-methylthreonine | Dmthr | D-α-methylthreonine |
| Mtrp | L-α-methyltryptophan | Dmtrp | D-α-methyltryptophan |
| Mtyr | L-α-methyltyrosine | Dmtyr | D-α-methyltyrosine |
| Mval | L-α-methylvaline | Dmval | D-α-methylvaline |
| Mnva | L-α-methylnorvaline | Ncbut | N-cyclobutylglycine |
| Metg | L-α-methylethylglycine | Nchep | N-cycloheptylglycine |

TABLE 2-continued

| Code | Non-conventional amino acid | Code | Non-conventional amino acid |
| --- | --- | --- | --- |
| Mtbug | L-α-methyl-t-butylglycine | Nchex | N-cyclohexylglycine |
| Mhphe | L-α-methyl-homophenylalanine | Ncdec | N-cyclodecylglycine |
| Manap | α-methyl-α-naphthylalanine | Ncdod | N-cyclododecylglycine |
| Mpen | α-methylpenicillamine | Ncoct | N-cyclooctylglycine |
| Mgabu | α-methyl-γ-aminobutyrate | Ncpro | N-cyclopropylglycine |
| Mchexa | α-methyl-cyclohexylalanine | Ncund | N-cycloundecylglycine |
| Mcpen | α-methyl-cyclopentylalanine | Naeg | N-(2-aminoethyl)glycine |
| Nnbhm | N-(N-(2,2-diphenylethyl) carbamylmethyl-glycine | Nbhm | N-(2,2-diphenylethyl)glycine |
| Nnbhe | N-(N-(3,3-diphenylpropyl) carbamylmethyl-glycine | Nbhe | N-(3,3-diphenylpropyl)glycine |
| Tic | 1,2,3,4-tetrahydroisoquinoline-3-carboxylic acid | Nmbc | 1-carboxy-1-(2,2-diphenyl ethylamino)cyclopropane |
| pThr | phosphothreonine | pSer | phosphoserine |
|  | O-methyl-tyrosine | pTyr | phosphotyrosine |
|  | hydroxylysine |  | 2-aminoadipic acid |

The peptides of some embodiments of the invention are preferably utilized in a linear form, although it will be appreciated that in cases where cyclization does not severely interfere with peptide characteristics, cyclic forms of the peptide can also be utilized.

Since the present peptides are preferably utilized in therapeutics or diagnostics which require the peptides to be in soluble form, the peptides of some embodiments of the invention preferably include one or more non-natural or natural polar amino acids, including but not limited to serine and threonine which are capable of increasing peptide solubility due to their hydroxyl-containing side chain.

Further contemplated modifications of the peptides of the present invention include C-terminal amidation.

In order to improve the bioavailability of the ERK peptides, a single, a portion or even all the amino acids in the peptide can be D amino acids which are not susceptible to enzymatic proteolytic activity and can improve altogether the use of the peptides of the invention as pharmaceuticals. The peptides of the present invention may be attached (either covalently or non-covalently) to a penetrating agent.

As used herein the phrase "penetrating agent" refers to an agent which enhances translocation of any of the attached peptide across a cell membrane.

According to one embodiment, the penetrating agent is a peptide and is attached to the ERK (either directly or non-directly) via a peptide bond. Preferably, the penetrating agent is attached to the N terminus of the ERK derived peptide.

Typically, peptide penetrating agents have an amino acid composition containing either a high relative abundance of positively charged amino acids such as lysine or arginine, or have sequences that contain an alternating pattern of polar/charged amino acids and non-polar, hydrophobic amino acids.

By way of a non-limiting example, cell penetrating peptide (CPP) sequences may be used in order to enhance intracellular penetration. CPPs may include short and long versions of the protein transduction domain (PTD) of HIV TAT protein, such as for example, YARAAARQARA (SEQ ID NO: 5), YGRKKRR (SEQ ID NO: 8), YGRKKRRQRRR (SEQ ID NO: 9), or RRQRR (SEQ ID NO: 10)]. However, the disclosure is not so limited, and any suitable penetrating agent may be used, as known by those of skill in the art.

When the peptides of the present invention are attached to cell penetrating peptides, it is contemplated that the full length peptide is no greater than 25 amino acids, no greater than 26 amino acids, no greater than 27 amino acids, no greater than 28 amino acids, no greater than 29 amino acids, or no greater than 30 amino acids.

Another method of enhancing cell penetration is via N-terminal myristoilation. In this protein modification, a myristoyl group (derived from myristic acid) is covalently attached via an amide bond to the alpha-amino group of an N-terminal amino acid of the peptide.

The peptides of some embodiments of the invention may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

A preferred method of preparing the peptide compounds of some embodiments of the invention involves solid phase peptide synthesis.

Large scale peptide synthesis is described by Andersson Biopolymers 2000; 55(3):227-50.

Since the peptides of the present invention are able to specifically inhibit the nuclear activities of ERK without modulating its cytoplasmic activities, these peptides may be used to inhibit ERK nuclear activities (e.g. proliferation) without harming other ERK-related cytoplasmic activities in the cells. Therefore, the peptides of this aspect of the present invention may serve as therapeutic agent for hyperproliferative diseases such as cancer without having the side-effects of other ERK inhibitors.

Thus, according to another aspect of the present invention there is provided a method of treating cancer in a subject in need thereof comprising administering to the subject a therapeutically effective amount of the peptides disclosed herein, thereby treating the cancer.

Examples of cancers that may be treated using the 19S-specific proteasome inhibitors of this aspect of the present invention include, but are not limited to adrenocortical carcinoma, hereditary; bladder cancer; breast cancer; breast cancer, ductal; breast cancer, invasive intraductal; breast cancer, sporadic; breast cancer, susceptibility to; breast cancer, type 4; breast cancer, type 4; breast cancer-1; breast cancer-3; breast-ovarian cancer; Burkitt's lymphoma; cervical carcinoma; colorectal adenoma; colorectal cancer; colorectal cancer, hereditary nonpolyposis, type 1; colorectal cancer, hereditary nonpolyposis, type 2; colorectal cancer, hereditary nonpolyposis, type 3; colorectal cancer, hereditary nonpolyposis, type 6; colorectal cancer, hereditary nonpolyposis, type 7; dermatofibrosarcoma protuberans; endometrial carcinoma; esophageal cancer; gastric cancer, fibrosarcoma, glioblastoma multiforme; glomus tumors, multiple; hepatoblastoma; hepatocellular cancer; hepatocellular carcinoma; leukemia, acute lymphoblastic; leukemia, acute myeloid; leukemia, acute myeloid, with eosinophilia; leukemia, acute nonlymphocytic; leukemia, chronic myeloid; Li-Fraumeni syndrome; liposarcoma, lung cancer; lung cancer, small cell; lymphoma, non-Hodgkin's; lynch cancer family syndrome II; male germ cell tumor; mast cell leukemia; medullary thyroid; medulloblastoma; melanoma, malignant melanoma, meningioma; multiple endocrine neoplasia; multiple myeloma, myeloid malignancy, predisposition to; myxosarcoma, neuroblastoma; osteosarcoma; ovarian cancer; ovarian cancer, serous; ovarian carcinoma; ovarian sex cord tumors; pancreatic cancer; pancreatic endocrine tumors; paraganglioma, familial nonchromaffin; pilomatricoma; pituitary tumor, invasive; prostate adenocarcinoma; prostate cancer; renal cell carcinoma, papillary, familial and sporadic; retinoblastoma; rhabdoid predisposition syndrome, familial; rhabdoid tumors; rhabdomyosarcoma; small-cell cancer of lung; soft tissue sarcoma, squamous cell carcinoma, basal cell carcinoma, head and neck; T-cell acute lymphoblastic leukemia; Turcot syndrome with glioblastoma; tylosis with esophageal cancer; uterine cervix carcinoma, Wilms' tumor, type 2; and Wilms' tumor, type 1, and the like.

According to a specific embodiment, the cancer is melanoma, breast cancer, lung cancer, prostate cancer or cervical cancer.

According to another embodiment, the melanoma is PLX4032 and/or U0126-resistant melanoma.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the peptides disclosed herein accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (peptide) effective to prevent, alleviate or ameliorate symptoms of a disorder (e.g., cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer, as further detailed below. Such information can be used to more accurately determine useful doses in humans.

Toxicity and therapeutic efficacy of the active ingredients described herein can be determined by standard pharmaceutical procedures in vitro, in cell cultures or experimental animals, as further detailed below. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to ensure blood or tissue levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

As mentioned, various animal models may be used to test the efficacy of the peptides of the present invention. A transgenic mouse model for cancer (e.g., breast cancer) such as the erb model (Shah N., et al., 1999, Cancer Lett. 146: 15-2; Weistein E J., et al., 2000, Mol. Med. 6: 4-16) or MTV/myc model (Stewart T A et al., 1984, Cell, 38: 627-637), the c-myc model (Leder A., et al., 1986, Cell, 45:485-495), v-Ha-ras or c-neu model (Elson A and Leder P, 1995, J. Biol. Chem. 270: 26116-22) can be used to test the ability of the peptides of the present invention to suppress tumor growth in vivo.

For the formation of solid tumors, athymic mice can be injected with human or animal (e.g., mouse) cancerous cells such as those derived from breast cancer, ovarian cancer, prostate cancer or thyroid cancer, and following the formation of cancerous tumors the mice can be subjected to intra-tumor and/or systemic administration of the peptides.

The following cell lines (provided with their ATCC Accession numbers) can be used for each type of cancer model:

For breast cancer:

Human breast cancer cell lines—MDA-MB-453 (ATCC No. HTB-131), MDA-MB-231 (ATCC No. HTB-26), BT474 (ATCC No. HTB-20), MCF-7 (ATCC No. HTB-22), MDA-MB-468.

For ovarian cancer:

Human ovarian cancer cell lines—SKOV3 (ATCC No. HTB-77), OVCAR-3 HTB-161), OVCAR-4, OVCAR-5, OVCAR-8 and IGROV1;

For prostate cancer:

Human prostate cancer cell lines—DU-145 (ATCC No. HTB-81), PC-3 (ATCC No.CRL-1435);

For thyroid cancer:

Human derived thyroid cancer cell lines—FTC-133, K1, K2, NPA87, K5, WR082-1, AR089-1, DRO81-1;

For lung cancer:

Mouse lung carcinoma LL/2 (LLCI) cells (Lewis lung carcinoma)—These cells are derived from a mouse bearing a tumor resulting from an implantation of primary Lewis lung carcinoma. The cells are tumorigenic in C57BL mice, express H-2b antigen and are widely used as a model for metastasis and for studying the mechanisms of cancer chemotherapeutic agents (Bertram J S, et al., 1980, Cancer Lett. 11: 63-73; Sharma S, et al. 1999, J. Immunol. 163: 5020-5028).

For melanoma:

Mouse B16-F10 cells (Melanoma)—The cells are derived from mouse (C57BL/6J) bearing melanoma (Briles E B, et al., 1978, J. Natl. Cancer Inst. 60: 1217-1222).

The cancerous cells can be cultured in a tissue culture medium such as the DMEM with 4 mM L-glutamine adjusted to contain 1.5 g/L sodium bicarbonate and 4.5 g/L glucose, supplemented with 10% fetal calf serum (FCS), according to known procedures (e.g., as described in the ATCC protocols).

Tumor formation in animal models by administration of cancerous cells—Athymic nu/nu mice (e.g., female mice) can be purchased from the Jackson Laboratory (Bar Harbor, Me.). Tumors can be formed by subcutaneous (s.c.) injection of cancerous cells (e.g., $2\times10^6$ cells in 100 µl of PBS per mouse). Tumors are then allowed to grow in vivo for several days (e.g., 6-14 days) until they reach a detectable size of about 0.5 cm in diameter. It will be appreciated that injection of cancerous cells to an animal model can be at the organ from which the cell line is derived (e.g., mammary tissue for breast cancer, ovary for ovarian cancer) or can be injected at an irrelevant tissue such as the rear leg of the mouse.

To test the effect of the peptides of the present invention on inhibition of tumor growth, the agents may be administered to the animal model bearing the tumor either locally at the site of tumor or systemically, by intravenous injection of infusion, via, e.g., the tail vein. The time of administration may vary from immediately following injection of the cancerous cell line (e.g., by systemic administration) or at predetermined time periods following the appearance of the solid tumor (e.g., to the site of tumor formation, every 3 days for 3-10 times as described in Ugen K E et al., Cancer Gene Ther. 2006 Jun. 9; [Epub ahead of print]).

It will be appreciated that administration may also be effected using a nucleic acid construct designed to express the peptide agent (e.g., a viral vector), naked pDNA and/or liposomes.

Tumor sizes are measured two to three times a week. Tumor volumes are calculated using the length and width of the tumor (in millimeters). The effect of the treatment can be evaluated by comparing the tumor volume using statistical analyses such as Student's t test. In addition, histological analyses can be performed using markers typical for each type of cancer.

According to another embodiment, the agents of the present invention are co-administered or co-formulated with other known chemotherapeutic agents and/or anti-inflammatory agents. In addition, they may be administered with other known therapies, including but not limited to chemotherapy, radiotherapy, phototherapy and photodynamic therapy, surgery, nutritional therapy, ablative therapy, combined radiotherapy and chemotherapy, brachiotherapy, proton beam therapy, immunotherapy, cellular therapy and photon beam radiosurgical therapy.

Examples of other chemotherapeutic agents which may be co-delivered/coformulated with the agents of the present invention include but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. Preferably, this term encompasses individuals who are at risk to develop the pathology.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990);

Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Peptides: The 4 peptides used were: (i) Scr—NILSQEL-PHSGDLQIG (SEQ ID NO: 1); (ii) SPS—GQLN-HILGILGSPSQED (SEQ ID NO: 2); (iii) APA—GQLN-HILGILGAPAQED (SEQ ID NO: 3); and (iv) EPE—GQLNHILGILGEPEQED (SEQ ID NO: 6). Each of them was conjugated in its N-terminal to either a modified TAT sequence (YARAAARQARA[22] SEQ ID NO: 5), or myristic acid[23] and C-terminally amidated. To study the rate of absorption, the SPS peptide was conjugated to lysine-biotin in their C-terminus. All peptides were purchased from "Peptide 2" (Chantilly, Va., USA), were more than 85% pure and kept as 100 mM DMSO stock solution at −20C, until used.

Cells: HeLa (derived from cervical cancer), MDA-MB-231 (Ras-transformed breast cancer), T47D (Her2 and Ras negative breast cancer), DU-145 and, PC-3 (prostate cancers) cells were grown in either DMEM or RPMI mediums with 10% fetal bovine serum (FBS). Immortalized, non-transformed, Chinese hamster ovary (CHO) cells were grown in DMEM/F-12+10% FBS. HCT-116 (colon cancer), UACC-62 (stable melanoma line with B-Raf and, many other oncogenic mutations), HOP62 (lung cancer), and NCI-H23 (lung cancer) cells were obtained from NCI-60 purchased by the Biological Service Unit of our Institute. Low passage (less than 10) primary melanoma cells with B-Raf mutation (A2185, A2352, A2024), and immortalized, non-transformed breast cells (HB2), were used. Established melanoma cell lines carrying B-Raf mutation (A2577, A2600, LOXIMVI) were from ATCC and A2058 cells were also used. All these melanoma cells were grown in RPMI supplemented with 10% FBS; and the HB2 cells were grown in the same medium supplemented with 10 μg/ml insulin and 0.5 μg/ml hydrocortisone. Immortalized, non-transformed breast MCF-10A cells (ATCC) were grown in DMEM/F12 with 5% donor horse serum, 20 ng/ml EGF, 10 μg/ml insulin, 0.5 μg/ml hydrocortisone, and 100 ng/ml cholera toxin (all reagents from Sigma, Israel).

Reagents and Antibodies: Tetradecanoyl phorbol acetate (TPA), EGF, Avidin-FITC and TGF-diamino-2-phenylindole (DAPI), 3,3'-Diaminobenzidine (DAB) were obtained from Sigma (St Louis, Mich.). Anti general Elk1 (gElk1) and gRSK1 Abs were from Santa Cruz Biotechnology (CA, USA). Anti pElk-1 (Ser383), PARP-1, pAKT (Ser473) and pRSK (Ser381) Abs were from Cell Signaling Technology (Beverly, Mass., USA). Anti Imp7 Ab was from Abnova (Taipei, Taiwan). Anti pERK (pTEY-ERK), gERK, gAKT, gp38, pp38 (TGY), gJNK and pJNK (TPY) Abs were from Sigma (Rehovot, Israel). Polyclonal and monoclonal anti phospho SPS-ERK Abs were produced in the Biological Service Unit of the Weizmann Institute of Science (Rehovot, Israel). Secondary fluorescent Ab conjugates were from Jackson Immunoresearch (West Grove, Pa.). Secondary Ab conjugated to peroxidase (Simple Stained Max PO) was from Nichirei Biosciences (Japan).

Fluorescence Microscopy: Cells were fixed in 3% paraformaldehyde in PBS (20 min, 23° C.), and then permeabilized and blocked with 0.2% Triton X-100 in PBS-BSA (2%) for 20 min at 23° C. The fixed cells were sequentially incubated with appropriated Abs, (diluted in 10 μg/ml BSA/PBS) for 1 h, followed by either Cy-2 or rhodamine-conjugated secondary Abs and DAPI (diluted in BSA/PBS, 1:200) for 1 h. To follow the subcellular localization of the biotin-conjugated peptides, cells were incubated with Avidin-FITC (diluted in BSA/PBS 1:400) and DAPI. Slides were analyzed and photographed by a fluorescent microscope (Nikon, Japan, 600× magnification).

Western Blotting and coimmunoprecipitation: (i) Preparation of cellular extracts for Western Blotting: Cells were rinsed twice with ice-cold PBS and scraped into Radio-immunoprecipitation assay buffer (RIPA; 137 mM NaCl, 20 mM Tris (pH 7.4), 10% glycerol, 1% Triton X-100, 0.5% deoxycholate, 0.1% SDS, 2 mM EDTA, 1 mM PMSF, and 20 μM leupeptin). The extracts were centrifuged (20,000×g, 15 min, 4° C.), and the supernatants were further analyzed by Western blotting. The blots were developed with horseradish peroxidase-conjugated anti-mouse or anti-rabbit Abs. (ii) Coimmunoprecipitation: Cells were rinsed twice with ice-cold PBS and scraped into buffer H (50 mM β-glycerophosphate (pH 7.3), 1.5 mM EGTA, 1 mM EDTA, 1 mM dithiothreitol, 0.1 mM sodium vanadate, 1 mM benzamidine, 10 μg/ml aprotinin, 10 μg/ml leupeptin, 2 μg/ml pepstatin). The extracts were sonicated (50 W, 2×7 sec), and centrifuged (15,000×g, 15 min, 4° C.). Cellular extracts were incubated overnight with the appropriate Abs preconjugated to A/G beads (1 h, 23° C.). Subsequently, the beads were washed ×3 with coimmunoprecipitation washing buffer (20 mM HEPES pH 7.4, 2 mM $MgCl_2$, 2 mM EGTA, 150 mM NaCl and 0.1% Triton-X-100) and once with PBS, and subjected to Western blot analysis.

Morphology and apoptosis (TUNEL) assays: Cells were seeded on glass cover slips in a 12-wells plate at 25% confluence with medium containing 1% of FCS. Peptides (EPE or Scr), DMSO, or U0126 in a final concentration of 10 μM, were added after 4 h (considered as time "0"). TUNEL staining was performed at 24 h after the treatment according to manufacturer instruction (Roche Applied Science, Nutley, N.J., USA). Briefly, the medium was removed and cells were fixed with 3% of paraformaldehyde (1.5 h, 23° C.). Cells were rinsed twice with PBS and permeabilized with 0.1% Triton X-100 and 0.1% sodium citrate for 2 min on ice. Cells were rinsed twice with PBS and 28 μl of TUNEL reaction mixture (25 μl of TUNEL label, 2.5 μl of TUNEL enzyme and 0.1 mg/ml of DAPI) was added directly on top of the slide, cells were incubated for 16 h in humid box at 37° C. Cover slips were rinsed three times with PBS and mounted on microscope slides. The slides were dried and then subjected to image acquisition by a florescence microscope. For morphology assay, the cells were seeded at approximately 25% confluence in 6 cm plates with medium containing 1% FCS. Peptides (EPE and Scr) or DMSO or U0126 in a final concentration of 10 μM, were added after 4 h (considered to be time 0), 24 h and 48 h. Images were obtained by a light microscope (Olympus BX51) after 72 h.

Proliferation assay: All cells, except of MCF-10A, were seeded into 12-well cell plates in 1% FBS medium. MCF-10A cells were seeded in their complete medium diluted 5 fold. DMSO, Scr peptide, EPE peptide, or U0126 (final concentration of 10 μM each) were added to the appropriated wells four hours later. Every day medium was changed to fresh one containing the same agents. The number of viable cells was measured by Methylene Blue assay at 72h after cell seeding. Shortly, cells were fixed with 4% Formaldehyde for 2 h at 23° C., washed once with 0.1M Borate Buffer pH 8.5 and stained with of 1% Methylene Blue in 0.1M Borate Buffer for 10 min. Color was extracted by adding 0.1M HCl for 3 h at 23° C., and examined at 595 nm. For time course experiments, viable cells were measured at 0, 24, 48, 72 and 96 h after cell seeding. For dose response experiments we treaded the cells with 0.1, 1, 3, 10, or 30 µM of peptides for 72 h, as described above.

Preparation and proliferation of inhibitors resistant melanoma cells: A2352 cells were supplemented with either PLX4032 (B-Raf inhibitor, 1 µM), or U0126 (MEK inhibitor, 10 µM) for 45 days. Cells that survived this inhibitory pressure were treated with the following agents: DMSO, Scr peptide, EPE peptide, U0126 (the final concentration of 10 µM each), PLX-4032 (1 µM), Wortmannin (PI3K inhibitor, 0.5 µM), or Taxol (25 ng/ml), and subjected to proliferation assay as described above.

Animal studies: All animal experiments were approved by the Animal Care and Use Committee of the Weizmann Institute of Science (Rehovot, Israel). Female CD-1 nude mice (Harlan), 5-6 weeks of age, were inoculated s.c. into the flank region with $2 \times 10^6$ MDA-MB-231, LOXIMVI, or HCT-116 cells in 150 µl PBS. Female SCID mice (Harlan), 5-6 weeks of age, were inoculated s.c. into the flank region with $10^7$ A2352 cells in 150 µl mixture of PBS with matrigel (2:1). Tumors were allowed to develop to the size of 5-6.5 mm in diameter (50~110 mm$^3$ volume) and then the animals were randomly allocated to different treatment groups. The peptides (100 mM stock in DMSO), were diluted to the necessary concentration in PBS and boiled for 5 minutes. Then, DMSO, Scr or EPE peptides were administered by i.v. injection into the tail vein (150 µl/mouse, 3 times a week). Tumor dimensions were measured with a digital sliding caliper. Tumor volume was calculated using the formula: $V = D_1 \times D_2 \times D_3 \times \pi/6$, where $D_1$, $D_2$, $D_3$—represent the three mutually orthogonal growth diameters. To assess any signs of systemic toxicity, body weight was monitored, and recorded at the end of the experiment.

Histology and immunohistochemistry: Tumor xenografts, lungs, livers, kidneys and hearts of animals from different treatment groups were removed and subjected for histological analysis by staining of 5 µm paraffin embedded tissue slides with H&E, and examination by light microscope. MDA-MB-231 and LOXIMVI tumor xenografts were subjected to immunohistochemical analysis using αgERK Abs. Briefly, paraffin embedded blocks of tumors after different treatments were cut at 4 µm thickness and stained with ERK Abs, followed by second antibodies conjugated to peroxidase and DAB staining. Representative fields of each specimen were photographed at ×20 and ×40 magnifications.

Statistical analysis: Digital images were processed with Adobe Photoshop 7.0 software. The statistical differences were analyzed using two-tailed t-Students test.

RESULTS

The EPE-peptide inhibits ERK's translocation: The nuclear translocation of ERK is a key step in mediating cellular proliferation, while having only minor influence on other cellular processes. It was found that the stimulated translocation of ERK requires the binding of its phosphorylated NTS with Imp7. To prevent this interaction, the present inventors used an NTS-derived peptide (GQLN-HILGILGSPSQED, SPS—SEQ ID NO: 2) that could compete with the binding. To be effective, the peptide would need to rapidly penetrate through the cell membrane and remain in the cytoplasm for a certain amount of time. To reach this goal, the present inventors examined two known ways to allow peptide penetration: modified viral TAT sequence [22] or myristic acid (Myr; [23]), both in the N-terminus of the peptide. Using biotinylated peptides with each of the leaders, it was found that both of them induced an efficient penetration into HeLa cells, but the Myr peptide remained in the cytoplasm longer than the peptide with the TAT sequence (FIGS. 7A-B).

Figure 1B:
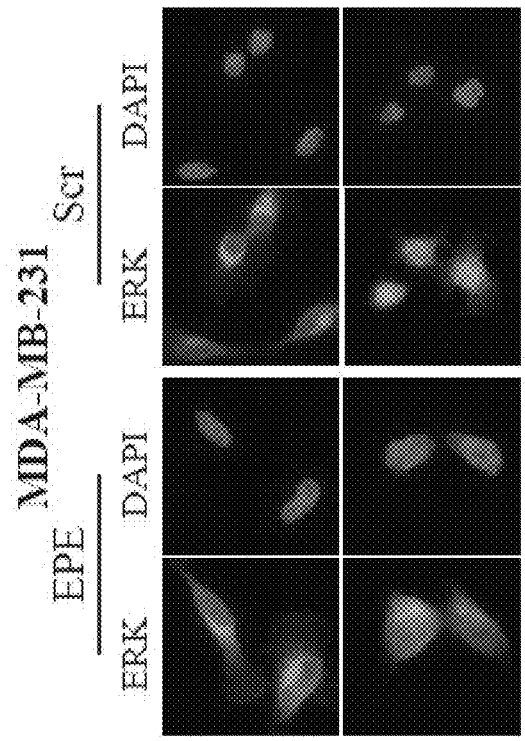
Figure 1A:
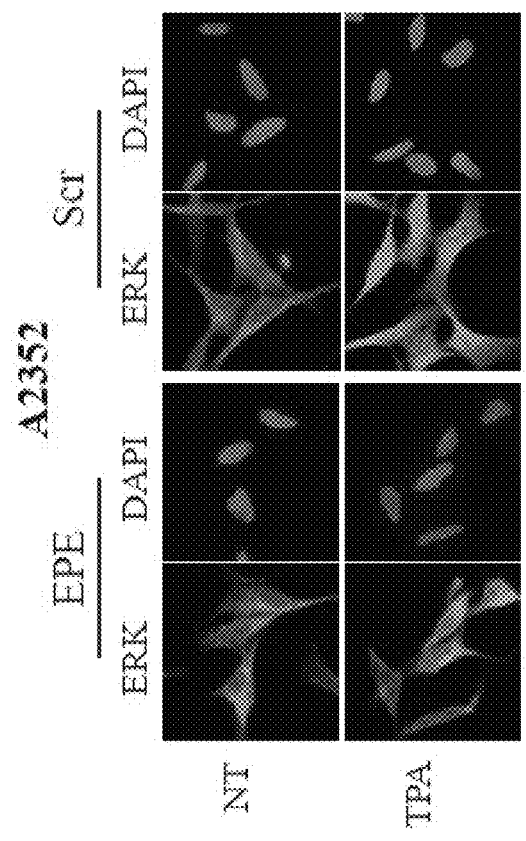

The present inventors then undertook to examine the effect of the peptide on the nuclear translocation of ERK1/2. Treatment of HeLa cells with the SPS peptide prevented TPA-induced nuclear translocation of ERK, which was similar to the inhibition by the MEK inhibitor U0126 (FIG. 1A). Next, the efficacy of the peptide was compared to similar peptides in which the SPS motif was replaced with either phosphomimetic (EPE) or nonphosphorylatable (APA) residues. The inhibitory effect of the EPE peptide was stronger than that of the other two (FIGS. 8A-B), probably because the EPE peptide better mimics the Imp7-bound ERK; The study was therefore continued with this peptide only. Repetition of the experiments with T47D, MDA-MB-231, A2352 cells and two immortalized non-transformed cells: melanocytes (NHEM-Ad) and breast (HB2) revealed a similar effect (FIGS. 1A-F), pointing to the generality of the effect. The same trend of inhibition was observed with subcellular fractionation as well (FIGS. 12A-D). No significant differences between the inhibition of ERK1 and ERK2 were observed (FIGS. 13A-C), In addition, the effect was specific to ERK, as the peptide affected neither the translocation of other MAPKs (FIGS. 9A-B), nor that of AKT (data not shown).

Molecular effects of the EPE peptide: Next, the present inventors undertook to identify the mechanism by which the EPE peptide prevents the nuclear translocation of ERK. As expected from the origin of the EPE-peptide, it was found that its addition to HeLa cells indeed prevented the interaction of Imp7 with ERK when examined by coimmunoprecipitation with anti Imp7 Abs (FIG. 2A). The effect of the peptide on the intracellular signaling of four distinct cell lines was examined. As expected, no effect of the peptide on cytoplasmic activities was detected, including either activatory ERK-TEY phosphorylation or the downstream activity of RSK (FIG. 2B). Moreover, even the NTS phosphorylation by CK2, which occurs in the cytosol, was only slightly affected despite the consensus CK2-phosphorylation site within the peptide. This lack of effect may suggest that the binding sites of CK2 and Imp7 to the NTS are not identical, and strongly support the specificity of the peptide to ERK-Imp7 interaction. Importantly, the peptide had no effect on the basal or stimulated phosphorylation of AKT, either shortly after stimulation, or in longer time periods after treatment (FIGS. 2E,F), indicating that the negative feedback loops of the cells were not affected by the peptide. Finally, although the peptide had no cytoplasmic effects, it did inhibit the phosphorylation of the transcription factor Elk1, which is a nuclear target of ERK1/2 (FIG. 2B), the phosphorylation of c-Myc (FIG. 2C) and, to a lesser extent, the expression and phosphorylation of c-Fos (FIGS. 14A-B). This effect on nuclear targets varied among the cell lines, (20-45% in Elk1, FIG. 2D), and was not so pronounced for c-Fos, probably due to the involvement of other, ERK1/2-independent, signaling components in some cells.

The EPE peptide effects in cultured cells: Given that the nuclear activity of ERK1/2 is critical for cell proliferation, the present inventors then examined the effect of the EPE peptide on proliferation/survival of different cancer-derived and immortalized cell lines. First, the optimal administration conditions of the EPE peptide (in which it presented the maximal effect on HeLa and T47D cells compared to a scrambled (Scr) peptide control) was found to be 10 µM, administered every 24 h in fresh medium (FIGS. 9A-B). Next, the present inventors examined the effect of the peptide on proliferation of different cell lines measured 72 h after peptide administration (FIG. 3A). Interestingly, the response of the different cells to the peptide can be categorized into four types. The first one was a profound reduction in cell number, which was observed in melanoma cells with oncogenic B-Raf (B-Raf melanoma). In the second group, including breast, prostate and cervical cancer-derived cells, the peptide prevented cell growth, but did not reduce the number of initial cells. The third group that included other melanomas, prostate and lung cancer-derived cells presented a small decrease in cell growth as compared to a peptide control, and a fourth group that included immortalized, non-transformed cells, did not respond to the peptide at all. Further comparison between the effects of EPE peptide and PLX4032 on the viability of some of the cell lines (FIG. 3B), revealed that in non-transformed melanocytes (NHEM-Ad) the EPE peptide does not have any significant effect despite the strong inhibitory effect of PLX4032. On the other hand, the EPE peptide was able to reduce the viability of N-Ras transformed melanoma cells LOXIMVI that are not sensitive to PLX4032 as was previously reported. In all other transformed cell lines examined, the effect of the EPE-peptide was at least as good, or even better, than that of PLX4032. Together, these results demonstrate the superior effects of the EPE peptide in treating various cancers without affecting the non-transformed cells.

EPE peptide effect on resistant melanoma cells: The major problem with the use of B-Raf and MEK inhibitors in the clinic is the development of drug-resistance after 6 to 8 months. Since the point of influence of the EPE peptide is downstream to the other two drugs, the present inventors examined whether it might affect melanoma cells resistant to the Raf and MEK inhibitors. For this purpose PLX-4032 and U0126 resistant cells were generated by adding the inhibitor to the A2352 melanoma line for 6 weeks. The surviving cells proliferated slower in the presence of the inhibitors, but regained normal growth when the inhibitors were removed. Using these cells, it was found that the EPE peptide was able to reduce cell growth, although this effect was not as impressive as observed in the non-resistant ones (FIG. 4A).

Similar effects were seen in two low-passage melanoma cells from vemurafenib-resistant patients (FIG. 4B). As expected, the EPE peptide reduced the amount of nuclear ERK1/2 both before and after stimulation (FIGS. 15A-B). No significant effects of the peptides were detected on the activation of AKT were detected (data not shown), indicating that the effects is not through the cytosolic negative feedback loops. Thus, the present results indicate that the resistant melanoma cells are highly responsive to the EPE peptide.

Since inhibition of the MAPK cascade often results in activation of negative feedback loops and stimulation of the PI3K/AKT pathway, this pathway was examined in the resistant cells as well. The results demonstrate no significant change in the influence of the PI3K inhibitor, indicating that the resistance was probably not due to the PI3K, and the EPE peptide operated via a distinct pathway. It was also demonstrated that the effect is not due to a change in the multidrug resistance system, as it was found that Taxol was as effective in non-resistant, as resistant cells. Thus, the present results strongly indicate that the EPE peptide is able to affect the resistant cells via inhibition of downstream machinery.

Figure 5A:
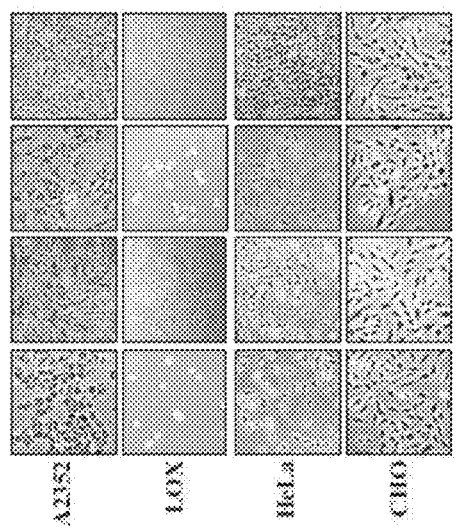
Figure 5B:
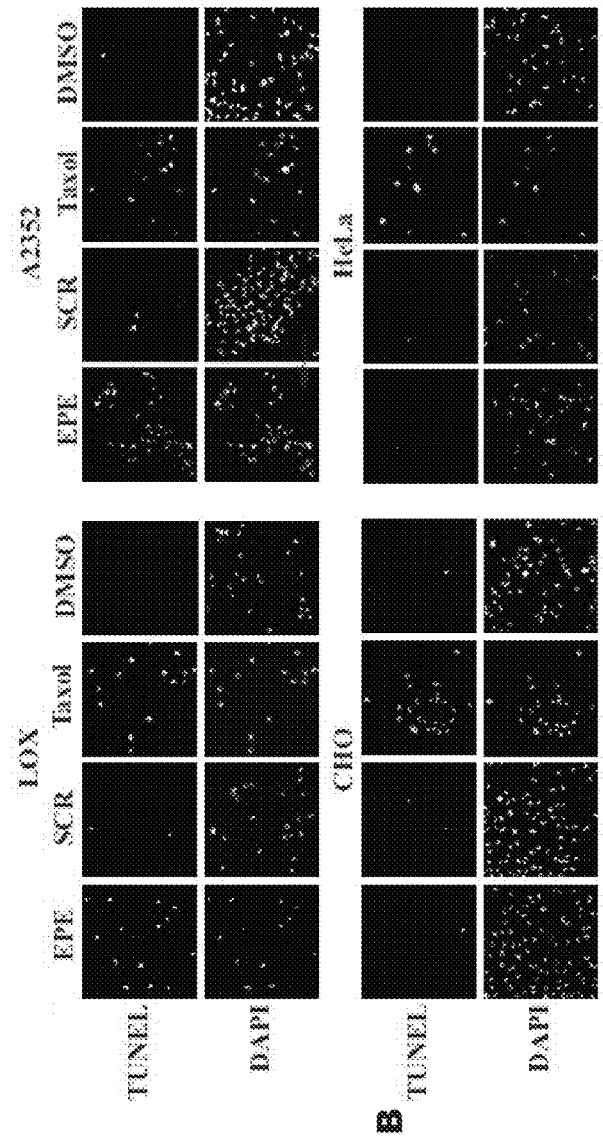
Figure 5C:
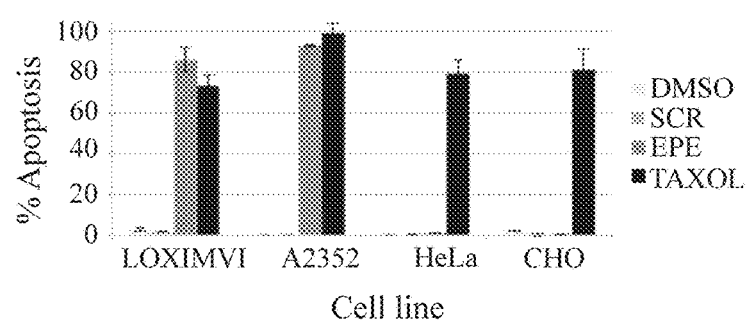
Figure 5D:
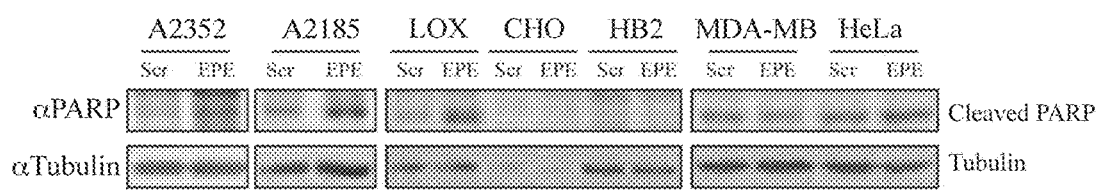

The EPE peptide induces apoptosis of melanoma: The effect of EPE peptide on cell morphology was visualized using light microscopy. While no effect was observed in most cell lines examined, the peptide did change the appearance of B-Raf melanoma cells by inducing cell-break already 24 hours after treatment (FIG. 5A). A similar appearance, albeit a weaker one, was observed with the MEK inhibitor U0126 as well, indicating that this effect is likely to be MEK/ERK-dependent. This change of morphology resembled cell death, which was previously reported to occur upon inhibition of the ERK cascade in B-Raf melanoma. Indeed, using TUNEL (FIGS. 5B,C) or PARP-1 (FIG. 5D) as marker for apoptosis, it was found that the morphology change correlated with an enhanced apoptosis. This apoptotic effect was specific to B-Raf mutated melanomas and, in these cells, was as strong as the apoptosis induced by Taxol. No apoptosis was detected in the other cell lines examined, despite their clear ability to undergo a Taxol or $H_2O_2$-induced cell death.

The EPE peptide effect on cancer xenografts: The present inventors then examined the effect of the EPE peptide on the growth of tumors in xenograft models (FIG. 6A). For this purpose, the tumors were allowed to grow to a size of ~60 $mm^3$ and only then the peptide was systemically administrated by injecting it in a proper formulation into the tail vein of the mice. Using such xenograft models in nude mice, dose dependent inhibition of the growth of MDA-MB-231, LOX-IMVI was noted, and to some extent, also on HCT-116. Remarkably, an even stronger effect of the peptide was seen with a xenograft of the low passage A2352 B-Raf melanoma in SCID mice. In this model, the peptide completely irradiated the melanoma within 2 weeks of tail vein administration. None of the animal treated exhibited any significant change in weight, organ morphology or other toxicity-related effects. Moreover, the treatment did not affect the size or structure of the kidneys, livers and hearts that were inspected at the end of the experiment. Interestingly, the structure of the lungs was not affected as well, although metastatic foci lungs in vehicle- and Scr peptide-treated were found, but not EPE peptide-treated mice (not shown).

In order to verify that the EPE peptide indeed operated by preventing the nuclear translocation, sections of xenograft tumors were excised from the treated animals at the end of the experiments, and stained with anti ERK antibody (Ab). As expected, it was found that EPE peptide did prevent such translocation in the treated MDA-MB-231 and LOXIMVI xenografts. In samples from the control treated xenografts, ERK was found all over the cells, with some preference to the nucleus, while in the EPE peptide-treated xenografts, ERK was localized almost exclusively in the cytoplasm (FIGS. 10A-B). These findings support the notion that the cytoplasmatic retention of ERK is the cause for the specific effect of the EPE peptide. Therefore, the prevention of the nuclear translocation of ERK1/2, which do not affect the cytoplasmic activity of the cascade, may serve as a good tool to prevent cancer growth, with less side-effects than the currently used inhibitors of the ERK1/2 cascade.

The major problem with the use of B-Raf and MEK inhibitors in the clinic is the development of resistance after 6 to 8 months, which results in tumor and metastasis recurrence. In order to study the recurrence of the disease after EPE peptide in comparison to PLX4032 treatment, mice bearing A2352 xenografts were treated with both reagents. Both treatments were proven beneficial in reducing the size of the initial ~80 mm3 tumors. Treatment of the EPE peptide resulted in a complete disappearance of the tumors of all mice within 10-23 days (FIG. 6B), while the PLX4032 treatment resulted in a complete disappearance in three mice (13-23 days after treatment), and two mice with small tumors. Following last treatment administration mice were kept for further follow up and evaluation of melanoma condition for up to 11 weeks. None of the EPE-peptide-treated mouse (N=7) showed any tumor recurrence, and all of them, as well as 5 other animals in a repeating experiment, remained healthy up to 11 weeks after treatment. On the other hand, as expected, in some (3 out of 5) of the PLX4032-treated mice, the tumor did recur, and one of them appeared to develop resistance within 13 days of treatment and exhibited a massive tumor growth thereafter. These results indicate that the EPE peptide treatment may prevent resistance and tumor recurrence better than that of PLX4032.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

Bibliography

1. Wortzel, I. & Seger, R. The ERK Cascade: Distinct Functions within Various Subcellular Organelles. *Genes Cancer* 2, 195-209, doi:10.1177/1947601911407328 (2011).
2. Keshet, Y. & Seger, R. The MAP kinase signaling cascades: a system of hundreds of components regulates a diverse array of physiological functions. *Methods Mol Biol* 661, 3-38, doi:10.1007/978-1-60761-795-2_1 (2010).
3. Morrison, D. K. MAP kinase pathways. *Cold Spring Harbor perspectives in biology* 4, doi:10.1101/cshperspect.a011254 (2012).
4. Plotnikov, A., Zehorai, E., Procaccia, S. & Seger, R. The MAPK cascades: Signaling components, nuclear roles and mechanisms of nuclear translocation. *Biochim Biophys Acta* 1813, 1619-1633, doi:S0167-4889(10)00322-8.
5. Osborne, J. K., Zaganjor, E. & Cobb, M. H. Signal control through Raf: in sickness and in health. *Cell Res* 22, 14-22, doi:10.1038/cr.2011.193 (2012).
6. Flaherty, K. T. et al. Inhibition of mutated, activated BRAF in metastatic melanoma. *N Engl J Med* 363, 809-819, doi:10.1056/NEJMoa1002011 (2010).
7. Flaherty, K. T. et al. Improved survival with MEK inhibition in BRAF-mutated melanoma. *N Engl J Med* 367, 107-114, doi:10.1056/NEJMoa1203421 (2012).
8. Su, F. et al. RAS mutations in cutaneous squamous-cell carcinomas in patients treated with BRAF inhibitors. *N Engl J Med* 366, 207-215, doi:10.1056/NEJMoa1105358 (2012).
9. Callahan, M. K. et al. Progression of RAS-mutant leukemia during RAF inhibitor treatment. *N Engl J Med* 367, 2316-2321, doi:10.1056/NEJMoa1208958 (2012).
10. Solit, D. B. & Rosen, N. Resistance to BRAF inhibition in melanomas. *N Engl J Med* 364, 772-774, doi:10.1056/NEJMcibr1013704 (2011).
11. Lito, P. et al. Relief of profound feedback inhibition of mitogenic signaling by RAF inhibitors attenuates their activity in BRAFV600E melanomas. *Cancer Cell* 22, 668-682, doi:10.1016/j.ccr.2012.10.009 (2012).
12. Mirzoeva, O. K. et al. Basal subtype and MAPK/ERK kinase (MEK)-phosphoinositide 3-kinase feedback signaling determine susceptibility of breast cancer cells to MEK inhibition. *Cancer Res* 69, 565-572 (2009).
13. Wee, S. et al. PI3K pathway activation mediates resistance to MEK inhibitors in KRAS mutant cancers. *Cancer Res* 69, 4286-4293 (2009).
14. Yao, Z. & Seger, R. The ERK signaling cascade—views from different subcellular compartments. *Biofactors* 35, 407-416 (2009).
15. Chen, R. H., Sarnecki, C. & Blenis, J. Nuclear localization and regulation of erk- and rsk-encoded protein kinases. *Mol Cell Biol* 12, 915-927 (1992).
16. Chuderland, D. & Seger, R. Protein-protein interactions in the regulation of the extracellular signal-regulated kinase. *Mol Biotechnol* 29, 57-74 (2005).
17. Chuderland, D., Konson, A. & Seger, R. Identification and characterization of a general nuclear translocation signal in signaling proteins. *Mol Cell* 31, 850-861 (2008).
18. Plotnikov, A., Chuderland, D., Karamansha, Y., Livnah, O. & Seger, R. Nuclear ERK translocation is mediated by protein kinase CK2 and accelerated by autophosphorylation. *Mol Cell Biol*, doi:MCB 0.05424-11
19. Zehorai, E., Yao, Z., Plotnikov, A. & Seger, R. The subcellular localization of MEK and ERK—a novel nuclear translocation signal (NTS) paves a way to the nucleus. *Mol Cell Endocrinol* 314, 213-220, doi:S0303-7207(09)00260-3.
20. Formstecher, E. et al. PEA-15 mediates cytoplasmic sequestration of ERK MAP kinase. *Dev Cell* 1, 239-250 (2001).
21. Casar, B., Pinto, A. & Crespo, P. ERK dimers and scaffold proteins: unexpected partners for a forgotten (cytoplasmic) task. *Cell Cycle* 8, 1007-1013 (2009).
22. Gomez-Cabrero, A. et al. Use of transduction proteins to target trabecular meshwork cells: outflow modulation by profilin I. *Mol Vis* 11, 1071-1082 (2005).
23. Nelson, A. R., Borland, L., Allbritton, N. L. & Sims, C. E. Myristoyl-based transport of peptides into living cells. *Biochemistry* 46, 14771-14781, doi:10.1021/bi701295k (2007).
24. Poulikakos, P. I. et al. RAF inhibitor resistance is mediated by dimerization of aberrantly spliced BRAF (V600E). *Nature* 480, 387-390, doi:10.1038/nature10662 (2011).
25. Jiang, C. C. et al. Apoptosis of human melanoma cells induced by inhibition of B-RAFV600E involves preferential splicing of bimS. *Cell death & disease* 1, e69, doi:10.1038/cddis.2010.48 (2010).
26. VanBrocklin, M. W., Verhaegen, M., Soengas, M. S. & Holmen, S. L. Mitogen-activated protein kinase inhibition induces translocation of Bmf to promote apoptosis in melanoma. *Cancer Res* 69, 1985-1994, doi:10.1158/0008-5472.CAN-08-3934 (2009).
27. Beck, D. et al. Vemurafenib Potently Induces Endoplasmic Reticulum Stress-Mediated Apoptosis in BRAFV600E Melanoma Cells. *Sci Signal* 6, raj, doi: 10.1126/scisignal.2003057 (2013).

28. Rapp, U. R., Gotz, R. & Albert, S. BuCy RAFs drive cells into MEK addiction. *Cancer Cell* 9, 9-12, doi:10.1016/j.ccr.2005.12.022 (2006).
29. Prahallad, A. et al. Unresponsiveness of colon cancer to BRAF(V600E) inhibition through feedback activation of EGFR. *Nature* 483, 100-103, doi:10.1038/nature10868 (2012).
30. Su, F. et al. Resistance to selective BRAF inhibition can be mediated by modest upstream pathway activation. *Cancer Res* 72, 969-978, doi:10.1158/0008-5472.CAN-11-1875 (2012).
31. Aksamitiene, E. et al. Prolactin-stimulated activation of ERK1/2 mitogen-activated protein kinases is controlled by PI3-kinase/Rac/PAK signaling pathway in breast cancer cells. *Cell Signal* 23, 1794-1805, doi:10.1016/j.cellsig.2011.06.014 (2011).
32. Zmajkovicova, K. et al. MEK1 Is Required for PTEN Membrane Recruitment, AKT Regulation, and the Maintenance of Peripheral Tolerance. *Mol Cell*, doi:10.1016/j.molcel.2013.01.037 (2013).
33. Smith, E. R. et al. Nuclear entry of activated MAPK is restricted in primary ovarian and mammary epithelial cells. *PLoS ONE* 5, e9295, doi:10.1371/journal.pone.0009295 (2010).

What is claimed is:

1. An isolated peptide being no longer than 20 amino acids comprising a sequence which is as set forth in SEQ ID NO: 4, wherein $X_1$ and $X_2$ are any amino acid, the peptide being capable of preventing extracellular signal-regulated kinase1/2 (ERK) translocation into the nucleus.

2. The isolated peptide of claim 1, being 17 amino acids long.

3. The isolated peptide of claim 1, wherein $X_1$ and $X_2$ are each independently selected from the group consisting of glutamic acid, aspartic acid, alanine and serine.

4. The isolated peptide of claim 1, wherein $X_1$ and $X_2$ are each independently selected from the group consisting of glutamic acid and aspartic acid.

5. The isolated peptide of claim 1, being devoid of the amino acid sequence Leu-Aspartic acid.

6. The isolated peptide of claim 1, wherein neither $X_1$ nor $X_2$ is alanine.

7. The isolated peptide of claim 1, consisting of the amino acid sequence selected from the group consisting of SEQ ID NOs: 2-3, 6 and 7.

8. A composition of matter comprising the isolated peptide of claim 1, attached to a cell penetrating agent.

9. The composition of matter of claim 8, wherein said cell penetrating agent comprises myristic acid.

10. A pharmaceutical composition comprising the peptide of claim 1 as the active agent and a pharmaceutically acceptable carrier.

11. The pharmaceutical composition of claim 10, wherein said peptide is attached to a cell penetrating agent.

12. A composition of matter comprising a peptide which is no longer than 30 amino acids comprising a sequence which is as set forth in SEQ ID NO: 4, wherein $X_1$ and $X_2$ are any amino acid, the peptide being capable of preventing extracellular signal-regulated kinase1/2 (ERK) translocation into the nucleus.

13. The composition of matter of claim 12, wherein said peptide comprises a heterologous cell penetrating peptide.

14. The composition of matter of claim 13, wherein said heterologous cell penetrating peptide comprises an amino acid sequence as set forth in SEQ ID NO: 5.

15. A method of treating a cancer which is associated with a disruption in ERK signaling in a subject in need thereof comprising administering to the subject a therapeutically effective amount of the composition of claim 12, thereby treating the cancer.

16. A pharmaceutical composition comprising the composition of claim 12 as the active agent and a pharmaceutically acceptable carrier.

17. The method of claim 16, wherein the cancer is selected from the group consisting of melanoma, breast cancer, lung cancer, prostate cancer and cervical cancer.

18. The method of claim 16, wherein the cancer is melanoma.

19. The method of claim 18, wherein said melanoma comprises B-Raf melanoma.

* * * * *

SEQUENCE LISTING

```
<160> NUMBER OF SEQ ID NOS: 10

<210> SEQ ID NO 1
<211> LENGTH: 16
<212> TYPE: PRT
<213> ORGANISM: Artificial sequence
<220> FEATURE:
<223> OTHER INFORMATION: Synthetic peptide (Scr)

<400> SEQUENCE: 1

Asn Ile Leu Ser Gln Glu Leu Pro His Ser Gly Asp Leu Gln Ile Gly
1               5                   10                  15

<210> SEQ ID NO 2
<211> LENGTH: 17
<212> TYPE: PRT
<213> ORGANISM: Artificial sequence
<220> FEATURE:
<223> OTHER INFORMATION: Synthetic peptide (SPS)

<400> SEQUENCE: 2

Gly Gln Leu Asn His Ile Leu Gly Ile Leu Gly Ser Pro Ser Gln Glu
1               5                   10                  15

Asp

<210> SEQ ID NO 3
<211> LENGTH: 17
<212> TYPE: PRT
<213> ORGANISM: Artificial sequence
<220> FEATURE:
<223> OTHER INFORMATION: Synthetic peptide (APA)

<400> SEQUENCE: 3

Gly Gln Leu Asn His Ile Leu Gly Ile Leu Gly Ala Pro Ala Gln Glu
1               5                   10                  15

Asp

<210> SEQ ID NO 4
<211> LENGTH: 17
<212> TYPE: PRT
<213> ORGANISM: Artificial sequence
<220> FEATURE:
<223> OTHER INFORMATION: A peptide capable of preventing extracellular
      signal-regulated kinase1/2 (ERK) translocation into the nucleus
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 4
```

```
Gly Gln Leu Asn His Ile Leu Gly Ile Leu Gly Xaa Pro Xaa Gln Glu
1               5                   10                  15
Asp

<210> SEQ ID NO 5
<211> LENGTH: 11
<212> TYPE: PRT
<213> ORGANISM: Artificial sequence
<220> FEATURE:
<223> OTHER INFORMATION: An example of a cell penetrating peptide (CPP)
      sequence

<400> SEQUENCE: 5

Tyr Ala Arg Ala Ala Ala Arg Gln Ala Arg Ala
1               5                   10

<210> SEQ ID NO 6
<211> LENGTH: 17
<212> TYPE: PRT
<213> ORGANISM: Artificial sequence
<220> FEATURE:
<223> OTHER INFORMATION: Synthetic peptide (EPE)

<400> SEQUENCE: 6

Gly Gln Leu Asn His Ile Leu Gly Ile Leu Gly Glu Pro Glu Gln Glu
1               5                   10                  15
Asp

<210> SEQ ID NO 7
<211> LENGTH: 17
<212> TYPE: PRT
<213> ORGANISM: Artificial sequence
<220> FEATURE:
<223> OTHER INFORMATION: Synthetic peptide (DPD)

<400> SEQUENCE: 7

Gly Gln Leu Asn His Ile Leu Gly Ile Leu Gly Asp Pro Asp Gln Glu
1               5                   10                  15
Asp

<210> SEQ ID NO 8
<211> LENGTH: 7
<212> TYPE: PRT
<213> ORGANISM: Artificial sequence
<220> FEATURE:
<223> OTHER INFORMATION: An example of a cell penetrating peptide (CPP)
      sequence

<400> SEQUENCE: 8

Tyr Gly Arg Lys Lys Arg Arg
1               5

<210> SEQ ID NO 9
<211> LENGTH: 11
<212> TYPE: PRT
<213> ORGANISM: Artificial sequence
<220> FEATURE:
<223> OTHER INFORMATION: An example of a cell penetrating peptide (CPP)
      sequence

<400> SEQUENCE: 9

Tyr Gly Arg Lys Lys Arg Arg Gln Arg Arg
1               5                   10
```

```
<210> SEQ ID NO 10
<211> LENGTH: 5
<212> TYPE: PRT
<213> ORGANISM: Artificial sequence
<220> FEATURE:
<223> OTHER INFORMATION: An example of a cell penetrating peptide (CPP)
      sequence

<400> SEQUENCE: 10

Arg Arg Gln Arg Arg
1               5
```